(12) United States Patent
McDevitt et al.

(10) Patent No.: US 9,307,977 B2
(45) Date of Patent: *Apr. 12, 2016

(54) METHOD AND APPARATUS FOR SECURING AN OBJECT TO BONE, INCLUDING THE PROVISION AND USE OF A NOVEL SUTURE ASSEMBLY FOR SECURING SUTURE TO BONE

(75) Inventors: Dennis McDevitt, Raleigh, NC (US);
Vincent Novak, Longmont, CO (US)

(73) Assignee: ConMed Corporation, Utica, NY (US)

( * ) Notice: Subject to any disclaimer, the term of this patent is extended or adjusted under 35 U.S.C. 154(b) by 170 days.

This patent is subject to a terminal disclaimer.

(21) Appl. No.: 13/093,634

(22) Filed: Apr. 25, 2011

(65) Prior Publication Data
US 2012/0116450 A1    May 10, 2012

Related U.S. Application Data

(60) Provisional application No. 61/410,027, filed on Nov. 4, 2010, provisional application No. 61/419,334, filed on Dec. 3, 2010, provisional application No. 61/422,859, filed on Dec. 14, 2010, provisional application No. 61/443,325, filed on Feb. 16, 2011.

(51) Int. Cl.
*A61B 17/04* (2006.01)
*A61B 17/17* (2006.01)
*A61B 17/00* (2006.01)

(52) U.S. Cl.
CPC ......... *A61B 17/0401* (2013.01); *A61B 17/1796* (2013.01); *A61B 17/0482* (2013.01); *A61B 2017/00429* (2013.01); *A61B 2017/0406* (2013.01); *A61B 2017/0409* (2013.01); *A61B 2017/0496* (2013.01)

(58) Field of Classification Search
CPC ........... A61B 17/0401; A61B 17/6166; A61B 17/0485; A61B 2017/06185; A61B 2017/0496; A61B 2017/0475; A61B 2017/06171; A61F 2002/0852; A61F 2002/0882; A61F 2002/0888
USPC .................................. 606/139, 142, 148, 228
See application file for complete search history.

(56) References Cited

U.S. PATENT DOCUMENTS

| 2,012,776 A | 8/1935 | Roeder |
| 3,580,256 A | 5/1971 | Wilkinson et al. |
| 5,217,470 A | 6/1993 | Weston |

(Continued)

FOREIGN PATENT DOCUMENTS

| CN | 1378439 | 11/2002 |
| CN | 101252887 | 8/2008 |

(Continued)

*Primary Examiner* — Alexander Orkin
(74) *Attorney, Agent, or Firm* — Pandiscio & Pandiscio

(57) ABSTRACT

A suture assembly including a first suture having a generally U-shaped configuration including a first arm, a second arm and a bridge connecting the first arm to the second arm; a second suture including a first arm, a second arm and a bridge connecting the first arm to the second arm; the first arm of the second suture being wrapped around the first arm of the first suture in a first direction, and the second arm of the second suture being wrapped around the second arm of the first suture in a second, opposite direction. The suture assembly being capable of assuming (i) a longitudinally-extended, radially-contracted first configuration, and (ii) a longitudinally-contracted, radially-expanded second configuration.

45 Claims, 51 Drawing Sheets

(56) References Cited

U.S. PATENT DOCUMENTS

| | | |
|---|---|---|
| 5,405,352 A | 4/1995 | Weston |
| 5,449,367 A | 9/1995 | Kadry |
| 5,549,630 A | 8/1996 | Bonutti |
| 5,584,862 A | 12/1996 | Bonutti |
| 5,665,110 A | 9/1997 | Chervitz et al. |
| 5,665,111 A | 9/1997 | Ray et al. |
| 5,718,717 A | 2/1998 | Bonutti |
| 5,728,114 A | 3/1998 | Evans et al. |
| 5,733,306 A | 3/1998 | Bonutti |
| 5,893,592 A | 4/1999 | Schulze et al. |
| 5,928,244 A | 7/1999 | Tovey et al. |
| 5,941,900 A | 8/1999 | Bonutti |
| 5,989,252 A | 11/1999 | Fumex |
| 6,056,773 A | 5/2000 | Bonutti |
| 6,077,292 A | 6/2000 | Bonutti |
| 6,086,604 A | 7/2000 | Fischell et al. |
| 6,110,183 A | 8/2000 | Cope |
| 6,113,611 A | 9/2000 | Allen et al. |
| RE36,974 E | 11/2000 | Bonutti |
| 6,143,006 A | 11/2000 | Chan |
| 6,179,860 B1 | 1/2001 | Fulton, III et al. |
| 6,203,572 B1 | 3/2001 | Johnson et al. |
| 6,287,325 B1 | 9/2001 | Bonutti |
| 6,325,816 B1 | 12/2001 | Fulton, III et al. |
| 6,409,742 B1 | 6/2002 | Fulton, III et al. |
| 6,500,184 B1 * | 12/2002 | Chan et al. ............... 606/144 |
| 6,503,267 B2 | 1/2003 | Bonutti et al. |
| 6,511,498 B1 | 1/2003 | Fumex |
| 6,524,317 B1 | 2/2003 | Ritchart et al. |
| 6,558,396 B1 | 5/2003 | Inoue |
| 6,712,849 B2 | 3/2004 | Re et al. |
| 6,758,855 B2 | 7/2004 | Fulton, III et al. |
| 6,767,037 B2 | 7/2004 | Wenstrom, Jr. |
| 6,972,027 B2 | 12/2005 | Fallin et al. |
| 7,048,754 B2 * | 5/2006 | Martin et al. ............... 606/232 |
| 7,153,312 B1 | 12/2006 | Torrie et al. |
| 7,303,575 B2 | 12/2007 | Ogle |
| 7,329,279 B2 | 2/2008 | Haug et al. |
| 7,347,863 B2 | 3/2008 | Rothe et al. |
| 7,390,332 B2 | 6/2008 | Selvitelli et al. |
| 7,491,212 B2 | 2/2009 | Sikora et al. |
| 7,494,496 B2 | 2/2009 | Swain et al. |
| 7,594,929 B2 | 9/2009 | Collette |
| 7,658,750 B2 | 2/2010 | Li |
| 7,658,751 B2 | 2/2010 | Stone et al. |
| 7,736,378 B2 | 6/2010 | Maahs et al. |
| 7,749,250 B2 | 7/2010 | Stone et al. |
| 7,857,830 B2 | 12/2010 | Stone et al. |
| 7,942,884 B2 | 5/2011 | Vahid et al. |
| 2002/0143359 A1 | 10/2002 | Fulton, III et al. |
| 2003/0167071 A1 | 9/2003 | Martin et al. |
| 2003/0191497 A1 | 10/2003 | Cope |
| 2004/0039442 A1 | 2/2004 | St. Goar et al. |
| 2004/0098050 A1 | 5/2004 | Foerster et al. |
| 2004/0167546 A1 | 8/2004 | Saadat et al. |
| 2004/0243171 A1 | 12/2004 | Fulton, III et al. |
| 2005/0187577 A1 | 8/2005 | Selvitelli et al. |
| 2005/0228448 A1 | 10/2005 | Li |
| 2005/0251157 A1 | 11/2005 | Saadat et al. |
| 2005/0251159 A1 | 11/2005 | Ewers et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251209 A1 | 11/2005 | Saadat et al. |
| 2005/0251210 A1 | 11/2005 | Westra et al. |
| 2005/0277981 A1 | 12/2005 | Maahs et al. |
| 2005/0277985 A1 | 12/2005 | Wert et al. |
| 2005/0283192 A1 | 12/2005 | Torrie et al. |
| 2006/0064126 A1 | 3/2006 | Fallin et al. |
| 2006/0190042 A1 | 8/2006 | Stone et al. |
| 2006/0212055 A1 | 9/2006 | Karabey et al. |
| 2007/0010857 A1 * | 1/2007 | Sugimoto et al. ............ 606/232 |
| 2007/0083236 A1 | 4/2007 | Sikora et al. |
| 2007/0162120 A1 | 7/2007 | Bouffier |
| 2007/0185532 A1 | 8/2007 | Stone et al. |
| 2007/0276433 A1 | 11/2007 | Huss |
| 2008/0009888 A1 | 1/2008 | Ewers et al. |
| 2008/0015594 A1 | 1/2008 | Ritchart et al. |
| 2008/0015635 A1 | 1/2008 | Olsen et al. |
| 2008/0015636 A1 | 1/2008 | Olsen et al. |
| 2008/0027446 A1 | 1/2008 | Stone et al. |
| 2008/0033487 A1 | 2/2008 | Schwartz et al. |
| 2008/0082128 A1 | 4/2008 | Stone |
| 2008/0086155 A1 | 4/2008 | Rothe et al. |
| 2008/0097522 A1 | 4/2008 | Chopra |
| 2008/0140092 A1 | 6/2008 | Stone et al. |
| 2008/0140093 A1 | 6/2008 | Stone et al. |
| 2008/0147086 A1 | 6/2008 | Pfister et al. |
| 2008/0147102 A1 | 6/2008 | Rotella et al. |
| 2008/0167658 A1 | 7/2008 | Kerr et al. |
| 2008/0177302 A1 | 7/2008 | Shurnas |
| 2008/0200930 A1 | 8/2008 | Saadat et al. |
| 2008/0208225 A1 | 8/2008 | Seibold et al. |
| 2008/0208226 A1 | 8/2008 | Seibold et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0255613 A1 | 10/2008 | Kaiser et al. |
| 2008/0269781 A1 | 10/2008 | Funamura et al. |
| 2008/0281355 A1 | 11/2008 | Mayer et al. |
| 2008/0312689 A1 | 12/2008 | Denham et al. |
| 2008/0319524 A1 | 12/2008 | Yachia et al. |
| 2009/0018561 A1 | 1/2009 | Schwartz et al. |
| 2009/0062846 A1 | 3/2009 | Ken |
| 2009/0062847 A1 | 3/2009 | Ken |
| 2009/0062848 A1 | 3/2009 | Ken |
| 2009/0062850 A1 | 3/2009 | Ken |
| 2009/0062854 A1 | 3/2009 | Kaiser et al. |
| 2009/0076547 A1 | 3/2009 | Sugimoto et al. |
| 2009/0082805 A1 | 3/2009 | Kaiser et al. |
| 2009/0182335 A1 | 7/2009 | Struhl |
| 2009/0312776 A1 | 12/2009 | Kaiser et al. |
| 2009/0318961 A1 * | 12/2009 | Stone et al. ............... 606/228 |
| 2010/0145384 A1 | 6/2010 | Stone et al. |
| 2010/0204730 A1 | 8/2010 | Maiorino et al. |
| 2010/0268275 A1 | 10/2010 | Stone et al. |
| 2011/0022083 A1 | 1/2011 | Dimatteo et al. |
| 2011/0022084 A1 | 1/2011 | Sengun et al. |
| 2011/0098727 A1 | 4/2011 | Kaiser et al. |
| 2011/0270278 A1 * | 11/2011 | Overes et al. ............... 606/144 |

FOREIGN PATENT DOCUMENTS

| | | |
|---|---|---|
| CN | 101961257 | 2/2011 |
| DE | 29 00 265 | 7/1980 |
| DE | 42 07 854 | 9/1993 |
| EP | 0 246 836 | 11/1987 |
| EP | 0 861 633 | 9/1998 |
| EP | 1 334 702 | 8/2003 |
| EP | 1 052 942 | 10/2004 |
| EP | 1 495 725 | 1/2005 |
| EP | 1 832 246 | 9/2007 |
| EP | 2 277 457 | 1/2011 |
| JP | 55-94247 | 7/1980 |
| JP | 4226643 | 8/1992 |
| JP | 05-016155 | 1/1993 |
| JP | 6-24533 | 4/1994 |
| JP | 07-328020 | 12/1995 |
| JP | 2006-25932 | 2/2006 |
| JP | 2006-025933 | 2/2006 |
| JP | 2006-25934 | 2/2006 |
| JP | 2011-25035 | 2/2011 |
| WO | WO 92/11810 | 7/1992 |
| WO | WO 95/22932 | 8/1995 |
| WO | WO 03/065903 | 8/2003 |
| WO | WO 03/096910 | 11/2003 |
| WO | WO 2004/006782 | 1/2004 |
| WO | WO 2005/011463 | 2/2005 |
| WO | WO 2006/037639 | 4/2006 |
| WO | WO 2006/039296 | 4/2006 |
| WO | WO 2006/082810 | 8/2006 |
| WO | WO 2006/111394 | 10/2006 |

(56) References Cited

FOREIGN PATENT DOCUMENTS

| WO | WO 2007/005394 | 1/2007 |
|----|----------------|--------|
| WO | WO 2008/010738 | 1/2008 |
| WO | WO 2008/048667 | 4/2008 |
| WO | WO 2009/029914 | 3/2009 |
| WO | WO 2010/105046 | 9/2010 |
| WO | WO 2011/137159 | 11/2011 |

* cited by examiner

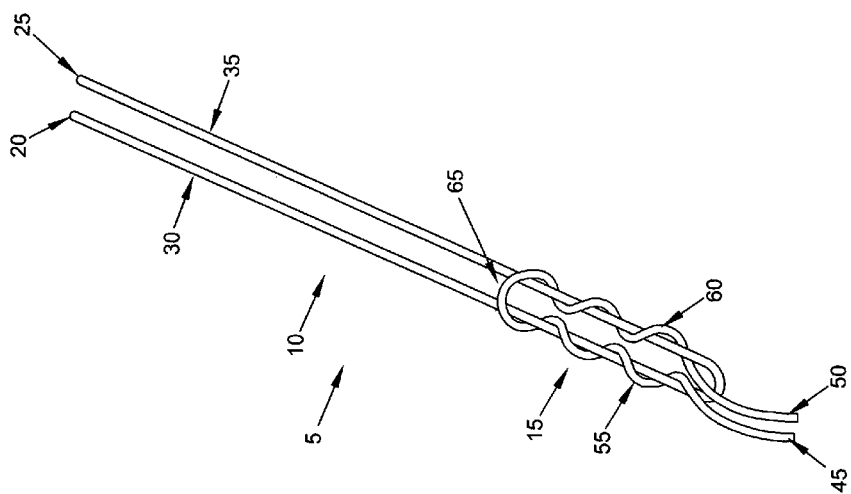
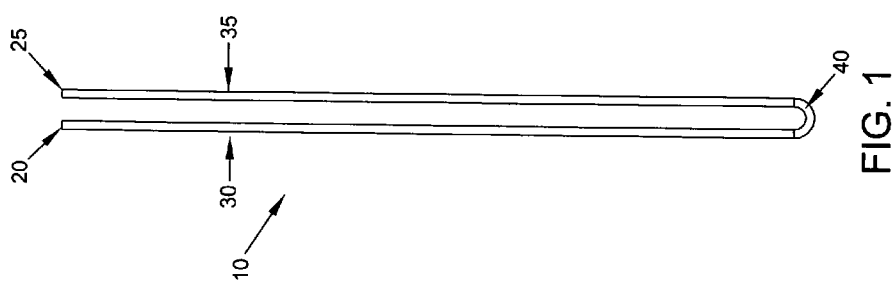

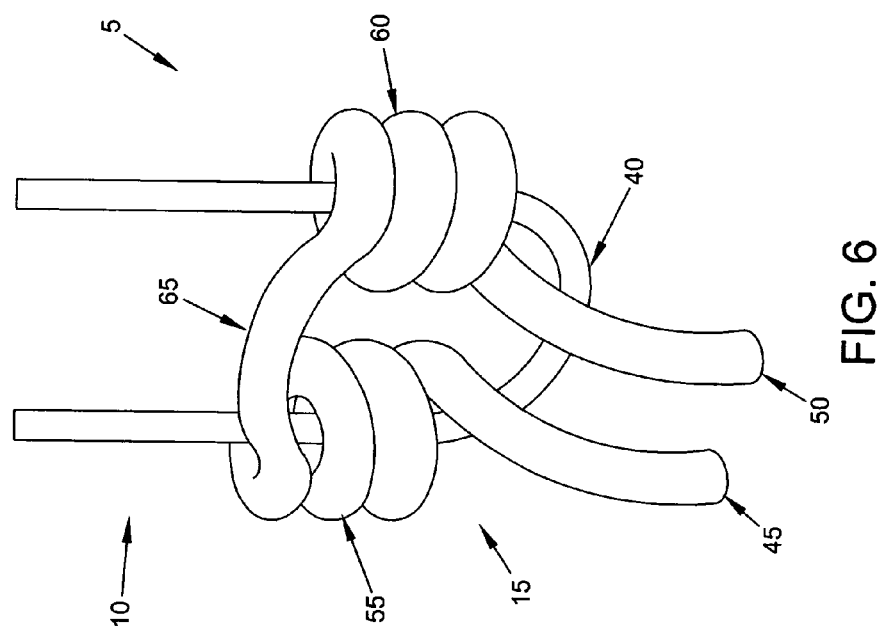
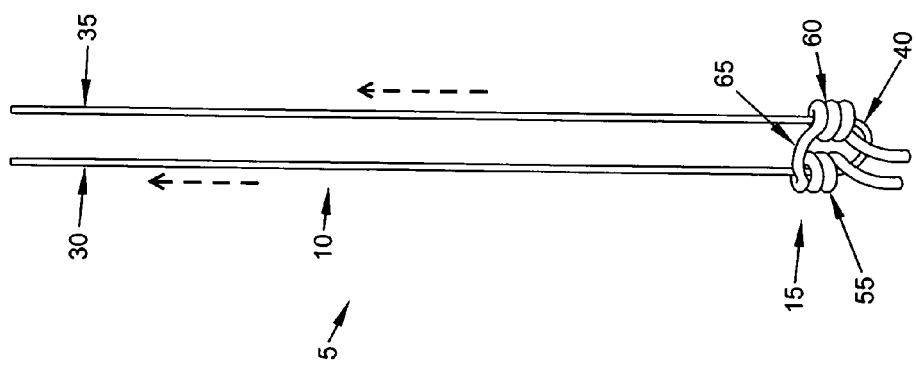

METHOD AND APPARATUS FOR SECURING AN OBJECT TO BONE, INCLUDING THE PROVISION AND USE OF A NOVEL SUTURE ASSEMBLY FOR SECURING SUTURE TO BONE

REFERENCE TO PENDING PRIOR PATENT APPLICATIONS

This patent application claims benefit of:

(i) prior U.S. Provisional Patent Application Ser. No. 61/410,027, filed Nov. 4, 2010 by Dennis McDevitt et al. for APPARATUS ASSEMBLY AND METHOD FOR SOFT TISSUE REPAIR;

(ii) prior U.S. Provisional Patent Application Ser. No. 61/419,334, filed Dec. 3, 2010 by Dennis McDevitt et al. for APPARATUS ASSEMBLY AND METHOD FOR SOFT TISSUE REPAIR;

(iii) prior U.S. Provisional Patent Application Ser. No. 61/422,859, filed Dec. 14, 2010 by Dennis McDevitt et al. for APPARATUS ASSEMBLY AND METHOD FOR SOFT TISSUE REPAIR; and (iv) prior U.S. Provisional Patent Application Ser. No. 61/443,325, filed Feb. 16, 2011 by Dennis McDevitt et al. for APPARATUS ASSEMBLY AND METHOD FOR SOFT TISSUE REPAIR.

The four (4) above-identified patent applications are hereby incorporated herein by reference.

FIELD OF THE INVENTION

This invention relates to surgical methods and apparatus in general, and more particularly to surgical methods and apparatus for securing an object to bone.

BACKGROUND OF THE INVENTION

Numerous devices are currently available to secure an object to bone. More particularly, screws, staples, cement and sutures have all been used to secure soft tissue (e.g., ligaments, tendons, muscles, etc.), bone and inanimate objects (e.g., prostheses) to bone.

In certain situations it can be desirable to attach a segment of a suture to bone, such that another segment of that suture can be used to secure an object (e.g., soft tissue) to the bone. This is generally accomplished by attaching a segment of the suture to a suture anchor, and then securing the suture anchor to the bone, such that the suture anchor attaches the suture to the bone. Then another segment of that suture can be used to secure an object (e.g., soft tissue) to the bone. In this respect it should be appreciated that it is common to attach a central segment of the suture to the suture anchor, so as to leave two free ends of the suture available for use in securing an object (e.g., soft tissue) to the bone.

Among other things, such suture anchors have found widespread application in procedures for re-attaching ligaments to bone, e.g., so as to restore a torn rotator cuff in the shoulder.

The aforementioned suture anchors generally comprise substantially rigid bodies to which the suture is attached, either at the time of manufacture or at the time of use. The substantially rigid bodies of the suture anchors may be formed out of a variety of materials (e.g., metal, plastic, bone, etc.) according to their particular form and function. By way of example but not limitation, a screw-type suture anchor is typically formed out of metal or plastic, a toggle-type suture anchor is typically formed out of plastic, an expansion-type suture anchor is typically formed out of plastic, etc. In any case, however, the body of the suture anchor is generally formed out of a substantially rigid material which must be reliably secured to the bone, whereby to reliably attach the suture to the bone.

Prior art suture anchors all suffer from one or more deficiencies. These deficiencies include, but are not limited to:

(i) various difficulties and/or inconveniences associated with a particular manner of securing the suture anchor to the bone (e.g., screw-type suture anchors require rotational motion, toggle-type suture anchors require toggling within a hole formed in the bone, expansion-type screw anchors require some sort of anchor deformation within a hole formed in the bone, etc.);

(ii) difficulties in ensuring that the body of the suture anchor is securely attached to the bone (e.g., toggle-type suture anchors can sometimes fail to properly set in a bone hole and may "skid" back out of the bone hole, expansion-type suture anchors may not expand properly within the bone hole and may pull back out of the bone hole, etc.);

(iii) complications associated with a possible failure of the suture anchor (and the possible subsequent migration of the substantially rigid body of the suture anchor out of the bone hole and into the working portion of a joint);

(iv) an inability to scale the suture anchor down to a size small enough to allow the suture anchor to be used in and around delicate anatomical structures;

(v) the need to form relatively large holes in the anatomy in order to secure the suture anchor to the bone;

(vi) inadequate holding power (e.g., limits to the holding strength which can be provided by a screw-type suture anchor, or the holding strength which can be provided by a toggle-type suture anchor, etc.); and/or (vii) inconveniences associated with attaching the suture to the suture anchor (either during manufacture or at the time of use), etc.

As a result, one object of the present invention is to provide a novel suture assembly for securing suture to bone.

Another object of the present invention is to provide a novel suture assembly for securing suture to bone which does not suffer from the deficiencies associated with the prior art.

Another object of the present invention is to provide a novel suture assembly for securing an object (e.g., soft tissue) to bone.

Another object of the present invention is to provide a novel method for securing an object (e.g., soft tissue) to bone.

SUMMARY OF THE INVENTION

These and other objects of the present invention are addressed by the provision and use of a novel suture assembly for securing suture to bone, such that the suture may be used to secure an object (e.g., soft tissue) to the bone.

In one preferred form of the present invention, there is provided a suture assembly comprising:

a first suture having a generally U-shaped configuration comprising a first arm, a second arm and a bridge connecting the first arm to the second arm;

a second suture comprising a first arm, a second arm and a bridge connecting the first arm to the second arm;

the first arm of the second suture being wrapped around the first arm of the first suture in a first direction, and the second arm of the second suture being wrapped around the second arm of the first suture in a second, opposite direction;

the suture assembly being capable of assuming (i) a longitudinally-extended, radially-contracted first configuration, and (ii) a longitudinally-contracted, radially-expanded second configuration.

In another preferred form of the present invention, there is provided a method for attaching an object to an anatomical structure, the method comprising:

providing a suture assembly comprising:

a first suture having a generally U-shaped configuration comprising a first arm, a second arm and a bridge connecting the first arm to the second arm;

a second suture comprising a first arm, a second arm and a bridge connecting the first arm to the second arm;

the first arm of the second suture being wrapped around the first arm of the first suture in a first direction, and the second arm of the second suture being wrapped around the second arm of the first suture in a second, opposite direction;

the suture assembly being capable of assuming (i) a longitudinally-extended, radially-contracted first configuration, and (ii) a longitudinally-contracted, radially-expanded second configuration;

inserting the suture assembly into an opening in the anatomical structure while the suture assembly is in its longitudinally-extended, radially-contracted first configuration, with the first and second arms of the first suture extending from the opening in the anatomical structure; and transforming the suture assembly from its longitudinally-extended, radially-contracted first configuration to its longitudinally-contracted, radially-expanded second configuration in order to secure the suture assembly to the anatomical structure.

In another preferred form of the present invention, there is provided a system for securing an object to an anatomical structure, the system comprising:

a suture assembly comprising:

a first suture having a generally U-shaped configuration comprising a first arm, a second arm and a bridge connecting the first arm to the second arm;

a second suture comprising a first arm, a second arm and a bridge connecting the first arm to the second arm;

the first arm of the second suture being wrapped around the first arm of the first suture in a first direction, and the second arm of the second suture being wrapped around the second arm of the first suture in a second, opposite direction;

the suture assembly being capable of assuming (i) a longitudinally-extended, radially-contracted first configuration, and (ii) a longitudinally-contracted, radially-expanded second configuration; and an inserter assembly for deploying the suture assembly in the anatomical structure, the inserter assembly comprising:

an insertion tube for carrying at least a portion of the suture assembly within the insertion tube when the suture assembly is in its longitudinally-extended, radially-contracted first configuration; and a push rod for engaging the suture assembly when the suture assembly is disposed within the insertion tube.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1 and 2 are schematic views showing how the novel suture assembly of the present invention is assembled;

FIGS. 5 and 6 are schematic views showing the novel suture assembly of FIG. 2 in a longitudinally-contracted, radially-expanded second configuration for lodging in a bone hole;

DETAILED DESCRIPTION OF THE PREFERRED EMBODIMENTS

The Novel Suture Assembly in General

Figure 4:
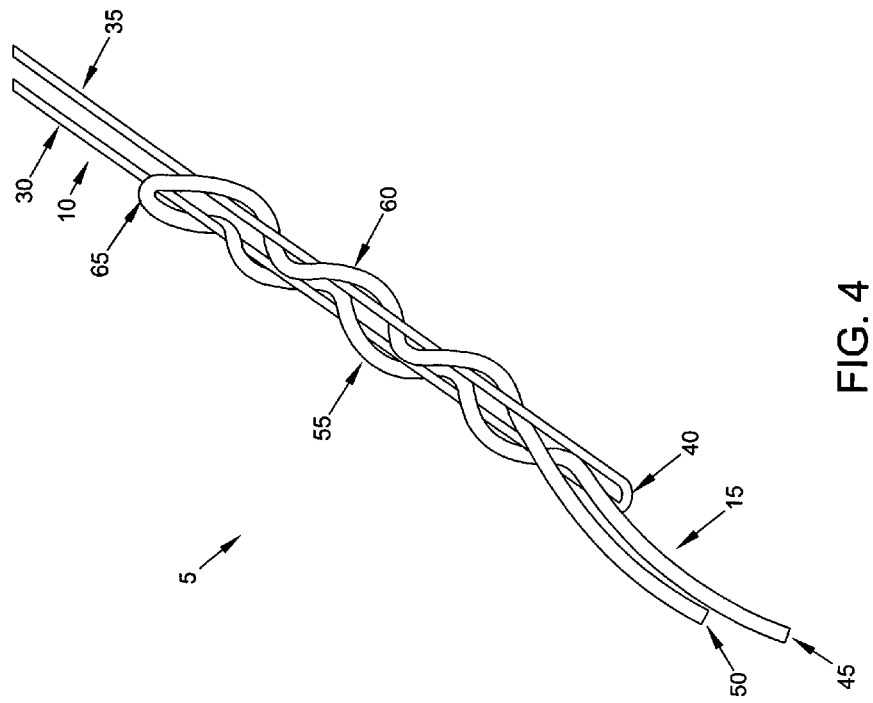
FIGS. 3 and 4 are schematic views showing the novel suture assembly of FIG. 2 in a longitudinally-expanded, radially-contracted first configuration for insertion into a bone hole.

Looking first at FIGS. 1 and 2, there is shown a novel suture assembly 5 for securing suture to bone, such that the suture may be used to secure an object (e.g., soft tissue) to the bone.

More particularly, novel suture assembly 5 generally comprises a first length of suture ("first suture") 10 (FIGS. 1 and 2) and a second length of suture ("second suture") 15 (FIG. 2).

First suture 10 comprises a first end 20 and second end 25 such that when first suture 10 is folded back on itself, it forms a first arm 30 which includes first end 20, and a second arm 35 which includes second end 25, with first arm 30 being connected to second arm 35 via a bridge 40.

Second suture 15 comprises a first end 45 and second end 50 such that when second suture 15 is folded back on itself, it forms a first arm 55 which includes first end 45, and a second arm 60 which includes second end 50, with first arm 55 being connected to second arm 60 via a bridge 65.

Second suture 15 is wrapped around first suture 10 by (i) folding second suture 15 back on itself so as to provide first arm 55 and second arm 60, with first arm 55 being connected to second arm 60 via a bridge 65; (ii) positioning bridge 65 of second suture 15 across first arm 30 and second arm 35 of first suture 10, with bridge 65 of second suture 15 being spaced from bridge 40 of first suture 10; and (iii) wrapping first arm 55 of second suture 15 around first arm 30 of first suture 10, and wrapping second arm 60 of second suture 15 around second arm 35 of first suture 10, in the manner shown in FIG. 2.

More particularly, first arm 55 of second suture 15 is wrapped around first arm 30 of first suture 10 in a first direction, and second arm 60 of second suture 15 is wrapped around second arm 35 of first suture 10 in a second, opposite direction. In other words, first arm 55 of second suture 15 is arranged in a first helical configuration about first arm 30 of first suture 10, and second arm 60 of second suture 15 is arranged in a second, oppositely wound helical configuration about second arm 35 of first suture 10. This opposite winding of first arm 55 and second arm 65 is a very significant aspect of the present invention, since it provides the novel suture assembly with a highly defined, appropriately shaped and consistently reproducible structure when the novel suture assembly is subsequently transformed from its longitudinally-expanded, radially-contracted first configuration into its longitudinally-contracted, radially-expanded second configuration, as will hereinafter be discussed in further detail.

In one preferred form of the present invention, first arm 55 of second suture 15 is wrapped three times around first arm 30 of first suture 10 in a clockwise direction (when viewed from the frame of reference of bridge 65), and second arm 60 of second suture 15 is wrapped three times around second arm 35 of first suture 10 in a countereclockwise direction (when viewed from the frame of reference of bridge 65), in the manner shown in FIG. 2.

In another preferred form of the present invention, first arm 55 of second suture 15 is wrapped four times around first arm 30 of first suture 10 in a clockwise direction (when viewed from the frame of reference of bridge 65), and second arm 60 of second suture 15 is wrapped four times around second arm 35 of first suture 10 in a countereclockwise direction (when viewed from the frame of reference of bridge 65).

And in another preferred form of the present invention, first arm 55 of second suture 15 is wrapped two times around first arm 30 of first suture 10 in a clockwise direction (when viewed from the frame of reference of bridge 65), and second arm 60 of second suture 15 is wrapped two times around second arm 35 of first suture 10 in a countereclockwise direction (when viewed from the frame of reference of bridge 65).

On account of the foregoing construction, novel suture assembly 5 can assume a first configuration in which second suture 15 is wrapped loosely around first suture 10, i.e., so that the suture assembly assumes a longitudinally-elongated, radially-contracted first configuration (FIGS. 3 and 4) which is suitable for insertion into a hole formed in bone. However, when first arm 30 and second arm 35 of first suture 10 are thereafter tensioned while holding bridge 65 of second suture 15 stationary (or by applying some other holding force to second suture 15, e.g., friction from the adjacent side wall of a bone hole containing suture assembly 5), suture assembly 5 can be transformed from the aforementioned longitudinally-elongated, radially-contracted first configuration into a longitudinally-contracted, radially-expanded second configuration (FIGS. 5 and 6) which is suitable for securing the suture assembly in the hole formed in bone. Significantly, and as will hereinafter be discussed in further detail, when novel suture assembly 5 is so disposed in a hole formed in bone, first arm 30 and second arm 35 of first suture 10 will extend out of the hole formed in the bone and be available for securing an object (e.g., soft tissue) to the bone.

And significantly, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6).

And significantly, the highly defined, appropriately shaped and consistently reproducible structure shown in FIGS. 5 and 6 is capable of carrying substantial loads without losing its defined shape when loads are applied to the first and second ends 20, 25 of first suture 10. As a result, when suture assembly 5 is inserted into a bone hole while in its longitudinally-expanded, radially-contracted first configuration and is thereafter transformed into its longitudinally-contracted, radially-expanded second configuration, novel suture assembly 5 will provide an excellent suture anchor with high holding strength.

Among other things, it should be appreciated that, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly.

In one preferred form of the present invention, first suture 10 comprises a first length of woven suture, and second suture 15 comprises a second length of woven suture.

Thus it will be seen that novel suture assembly 5 constitutes an all-suture construct which can assume (i) a longitudinally-expanded, radially-contracted first configuration for insertion into a hole formed in a bone, and (ii) a longitudinally-contracted, radially-expanded second configuration for lodging in the hole formed in the bone, with the suture assembly providing a pair of free suture arms extending out of the hole formed in the bone for use in securing an object (e.g., soft tissue) to the bone. Significantly, by forming the novel suture assembly 5 in the specific manner discussed above, the longitudinally-contracted, radially-expanded second configuration of the suture assembly constitutes a highly defined, appropriately shaped and consistently reproducible structure which is able to carry substantial loads without losing its defined shape, whereby to provide a suture anchor with high holding strength. And significantly, by forming the novel suture assembly 5 in the specific manner discussed above, the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly.

Novel Inserter Assembly for Deploying the Novel Suture Assembly in Bone

Looking next at FIGS. 7-11, there is shown an inserter assembly 70 and associated cannulated drill guide assembly 75 which may be used to deploy novel suture assembly 5 in bone. Inserter assembly 70 in turn comprises an insertion tube assembly 80 and a push rod assembly 85.

More particularly, cannulated drill guide assembly 75 generally comprises an elongated drill guide tube 86 having a distal end 90 carrying distal end prongs 95, and a proximal end 100 carrying a drill guide handle 105. A lumen 106 extends through elongated drill guide tube 86 and drill guide handle 105.

Insertion tube assembly 80 generally comprises an elongated insertion tube 107 having a distal end 110 sized to receive novel suture assembly 5 (either loosely or, more preferably, tightly compressed) when the novel suture assembly is in its aforementioned longitudinally-expanded, radially-contracted first configuration (FIGS. 3, 4, 10 and 11). Elongated insertion tube 107 of insertion tube assembly 80 also comprises a proximal end 115 carrying an insertion tube handle 120. A lumen 121 extends through elongated tube insertion 107 and insertion tube handle 120.

Push rod assembly 85 generally comprises a push rod 122 having a distal end 125 terminating in a distal end surface 130, and a proximal end 135 carrying a push rod handle 140.

Insertion tube assembly 80 is sized so that its elongated insertion tube 107 can be received within lumen 106 of cannulated drill guide assembly 75 such that, when cannulated drill guide assembly 75 is used to form a hole in a bone, the distal end of insertion tube assembly 80 can be delivered to that hole in a bone, as will hereinafter be discussed.

Push rod assembly 85 is sized so that its push rod 122 can be slidably received within lumen 121 of insertion tube assembly 80 such that, when novel suture assembly 5 is disposed within the distal end 110 of elongated insertion tube 107 of insertion tube assembly 80, advancement of push rod assembly 85 relative to insertion tube assembly 80, and/or retraction of insertion tube assembly 80 while holding push rod assembly 85 stationary, will cause novel suture assembly 5 to be released from distal end 110 of elongated insertion tube 107 of insertion tube assembly 80, as will hereinafter be discussed. Once novel suture assembly 5 has been released from distal end 110 of elongated insertion tube 107 of insertion tube assembly 80, tensioning first arm 30 and second arm 35 of first suture 10, while push rod assembly 85 holds bridge 65 of second suture 15 from moving proximally, will cause novel suture assembly 5 to transform from its longitudinally-elongated, radially-contracted first configuration (FIGS. 3, 4, 10 and 11) into its longitudinally-contracted, radially-expanded second configuration (FIGS. 5 and 6).

Insertion tube assembly 80 is also sized so that its lumen 121 will accommodate first and second arms 30, 35 of first suture 10 alongside push rod 122 of push rod assembly 85 when push rod 122 is disposed in lumen 121 of insertion tube assembly 80.

Novel suture assembly 5 is intended to be disposed within the distal end of insertion tube assembly 80, distal to push rod assembly 85, with first arm 30 and second arm 35 of first suture 10 extending out the proximal end of inserter assembly 70 via lumen 121 of insertion tube assembly 80, with first arm 30 and second arm 35 of first suture 10 extending alongside push rod 122 of push rod assembly 85. Preferably novel suture assembly 5 is tightly compressed within the distal end of insertion tube assembly 80, so as to provide the largest possible differential between the diameter of the radially-elongated, radially-contracted first configuration (FIGS. 3, 4, 10 and 11) and the longitudinally-contracted, radially-expanded second configuration (FIGS. 5 and 6), whereby to minimize the size of the bone hole and thereby increase holding power in the bone. In this respect it should be appreciated that by winding first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively, it is possible for the first and second sutures 10, 15 to "self-accommodate" within the interior of insertion tube assembly 80, thereby permitting maximum compression of the novel suture assembly within the insertion tube assembly. Furthermore, by leaving first end 45 and second end 50 of second suture 15 free (i.e., unconnected) relative to one another, the first and second sutures 10, 15 can further self-accommodate within the interior of insertion tube assembly 80, thereby permitting maximum compression of the novel suture assembly within the insertion tube assembly. Thus it will be appreciated that, by forming novel suture assembly 5 in the specific manner discussed above, the suture assembly is capable of self-accommodating itself into the smallest possible diameter within the insertion tube assembly, thereby permitting maximum compression of the novel suture assembly within the insertion tube assembly, and hence permitting use of a smaller bone hole and thus providing maximum holding power within the bone.

Using the Novel Suture Assembly to Secure Suture to Bone, in Order to Secure an Object to Bone Novel suture assembly 5 may be used to secure suture to bone, such that the suture may be used to secure an object (e.g., soft tissue) to the bone.

In one preferred form of the invention, inserter assembly 70 and its associated cannulated drill guide assembly 75 may be used to deploy novel suture assembly 5 in bone, in order to secure an object to bone.

More particularly, in one preferred form of the present invention, and looking now at FIGS. 12-18, the distal end of cannulated drill guide assembly 75 is first placed against the surface of a bone 145 (FIG. 12) which is to have suture secured thereto. As this occurs, prongs 95 on the distal end of cannulated drill guide assembly 75 help stabilize the cannulated drill guide assembly against the bone. Then a bone drill (not shown) of the sort well known in the art is advanced through lumen 106 of the cannulated drill guide assembly 75 and into the bone so that a bone hole 150 of appropriate size (diameter and depth) is formed in the bone. Note that bone hole 150 extends through the cortical layer 155 of bone 145 and into the cancellous region 160 of the bone. Then the bone drill is removed from cannulated drill guide assembly 75 while leaving the drill guide in position against bone 145.

Figure 13:
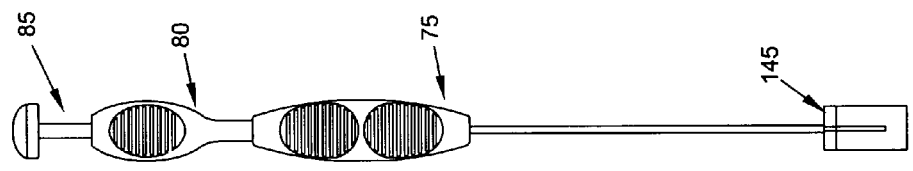
Figure 14:
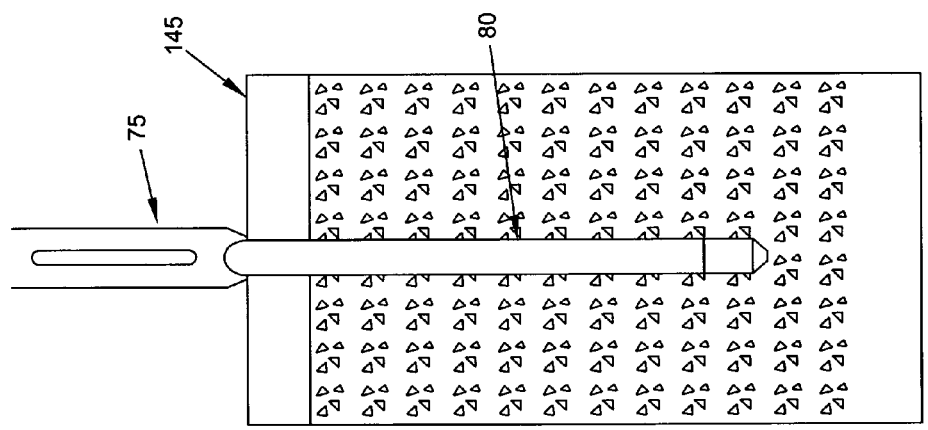

Next, the distal end 110 of insertion tube assembly 80, carrying novel repair contruct 5 therein, is advanced through cannulated drill guide assembly 75 and into bone hole 150 formed in bone 145 (FIGS. 13 and 14). Preferably, push rod 122 of push rod assembly 85 is already disposed within lumen 121 of insertion tube assembly 80 as this occurs, with distal end 130 of push rod assembly 85 sitting against bridge 65 of second suture 15. Alternatively, push rod 122 of push rod assembly 85 can be inserted into lumen 121 of insertion tube assembly 80 after the distal end of insertion tube assembly 80 has been inserted into bone hole 150 so that distal end 130 of push rod assembly 85 sits against bridge 65 of second suture 15.

Figure 15:
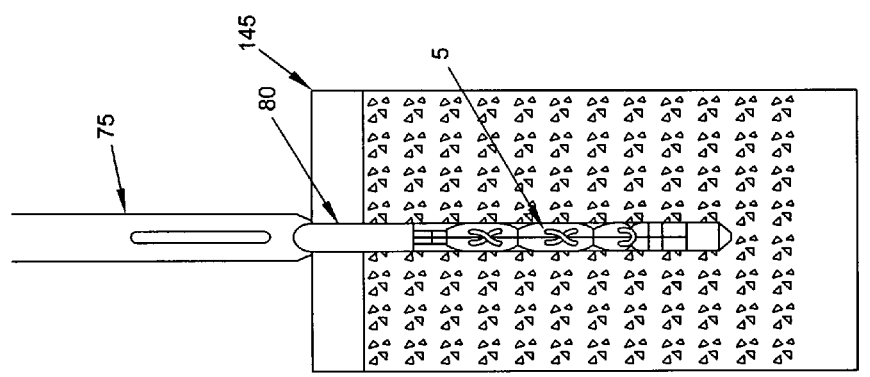
Figure 16:
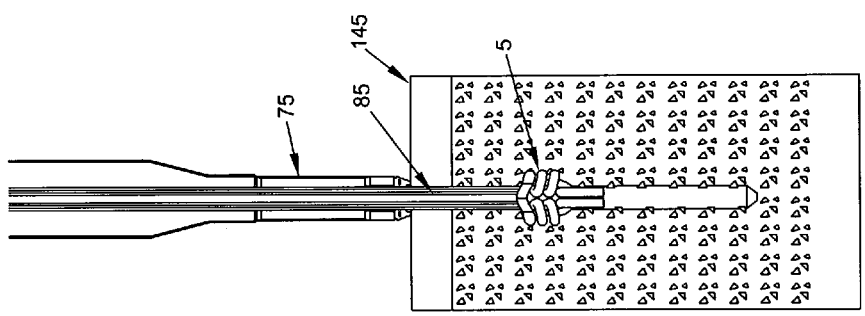
Figure 17:
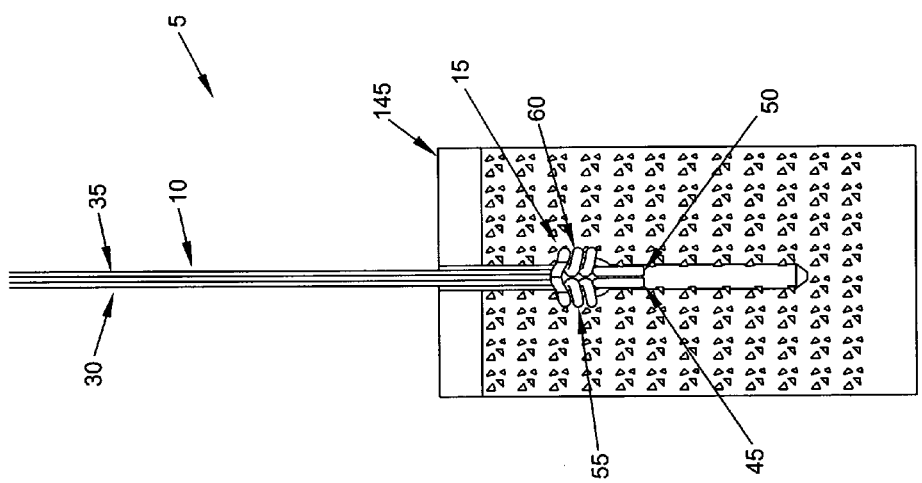
Figure 18:
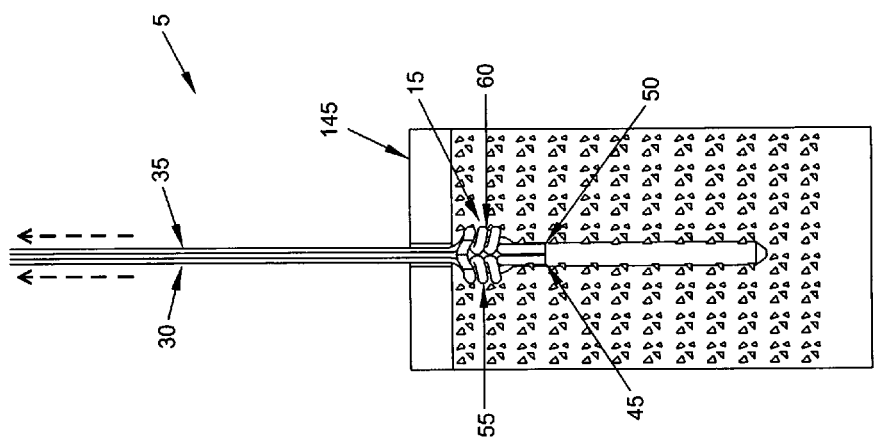

Next, insertion tube assembly 80 is retracted while holding distal end 130 of push rod assembly 85 stationary, so that novel suture assembly 5 is released from the distal end 110 of insertion tube assembly 80 (FIG. 15).

Then, with push rod assembly 85 still in position against bridge 65 of second suture 15, first arm 30 and second arm 35 of first suture 10 are tensioned, thereby transforming novel suture assembly 5 from its longitudinally-extended, radially-contracted first configuration into its longitudinally-contracted, radially-expanded second configuration (FIG. 16), whereby to expand novel suture assembly 5 laterally into the cancellous region 160 of bone 145.

At this point, inserter assembly 70 and cannulated drill guide assembly 75 are removed from the surgical site (FIG. 17), and first arm 30 and second arm 35 of first suture 10 are tensioned further so as to further laterally expand novel suture assembly 5 and cause the laterally-expanded novel suture assembly to seat against the underside of cortical layer 155 of bone 145 (FIG. 18), whereby to secure the novel suture assembly 5 within bone hole 150 (FIG. 18), with first arm 30 and second arm 35 of first suture 10 extending out of the bone hole.

Significantly, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6).

And significantly, the highly defined, appropriately shaped and consistently reproducible structure shown in FIGS. 5 and 6 is capable of carrying substantial loads without losing its defined shape when loads are applied to the first and second ends 20, 25 of first suture 10. As a result, when suture assembly 5 is inserted into a bone hole while in its longitudinally-expanded, radially-contracted first configuration and is thereafter transformed into its longitudinally-contracted, radially-expanded second configuration, novel suture assembly 5 will provide an excellent suture anchor with high holding strength.

Thereafter, one or both of first arm 30 and second arm 35 of first suture 10 may be used to secure an object (e.g., soft tissue) to the bone. By way of example but not limitation, one or both of first arm 30 and second arm 35 may be passed through a piece of soft tissue (e.g., a ligament) and then tied together so as to secure the soft tissue to bone.

Significantly, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly. As a result, if at any time it should be desired to remove the novel suture assembly 5 from bone hole 150, first arm 30 of first suture 10, or second arm 35 of first suture 10, is simply pulled away from second suture 15, whereby to "undo" the suture assembly. Once first suture 10 has been pulled clear of the surgical site, second suture 15 may be extracted from bone hole 150 (e.g., with a narrow suture grasper) and removed from the surgical site.

Figure 19:
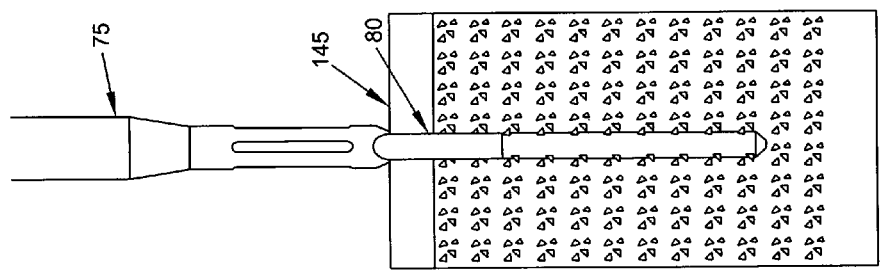
FIGS. 19-26 are schematic views showing another manner in which the inserter assembly and associated cannulated drill guide assembly of FIG. 7 can be used to deploy the novel suture assembly of FIG. 2 in a bone, with FIG. 26 showing the novel suture assembly released from the inserter assembly and in its longitudinally-contracted, radially-expanded second configuration so as to be secured to the bone.
Figure 20:
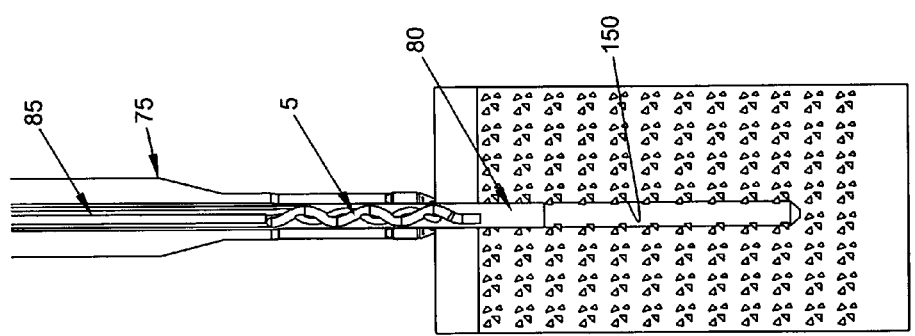

In another preferred form of the present invention, and looking now at FIGS. 19-26, the distal end of cannulated drill guide assembly 75 is first placed against the surface of bone 145, then a bone drill (not shown) is advanced through lumen 106 of the cannulated drill guide assembly 75 and into the bone so that a bone hole 150 of appropriate size (diameter and depth) is formed in the bone, then the bone drill is removed from cannulated drill guide assembly 75 while leaving the cannulated drill guide assembly in position against bone 145, and then the distal end 110 of insertion tube assembly 80, carrying novel suture assembly 5 therein, is advanced through cannulated drill guide assembly 75 and into bone hole 150 formed in bone 145 (FIGS. 19 and 20). Preferably, push rod 122 of push rod assembly 85 is already disposed within lumen 121 of insertion tube assembly 80 as this occurs, with distal end 130 of push rod assembly 85 sitting against bridge 65 of second suture 15. Alternatively, push rod 122 of push rod assembly 85 can be inserted into lumen 121 of insertion tube assembly 80 after the distal end of insertion tube assembly 80 has been inserted into bone hole 150 so that distal end 130 of push rod assembly 85 sits against bridge 65 of second suture 15.

Figure 21:
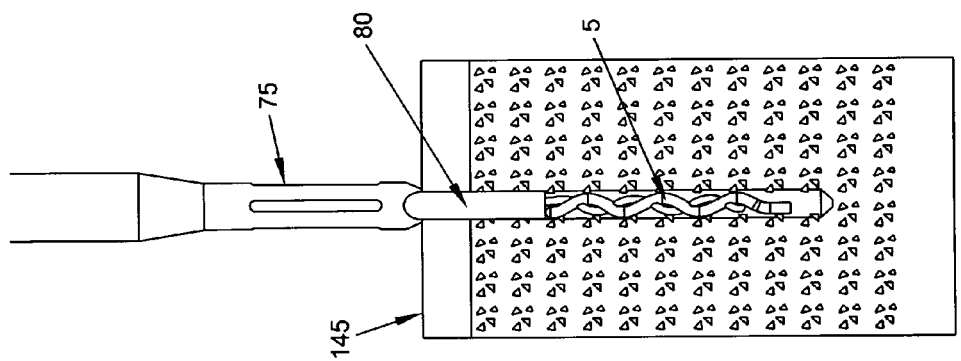
Figure 22:
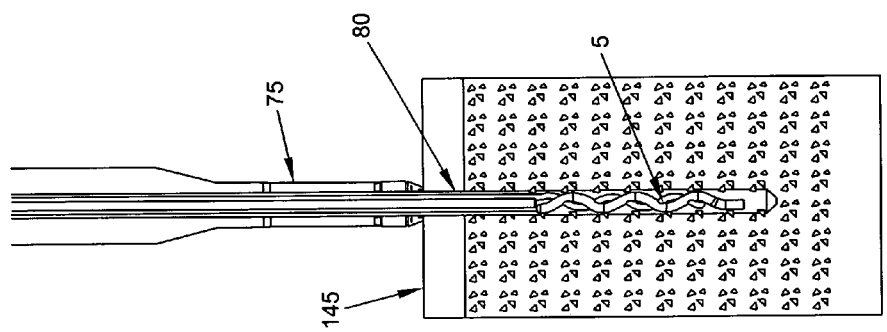
Figure 23:
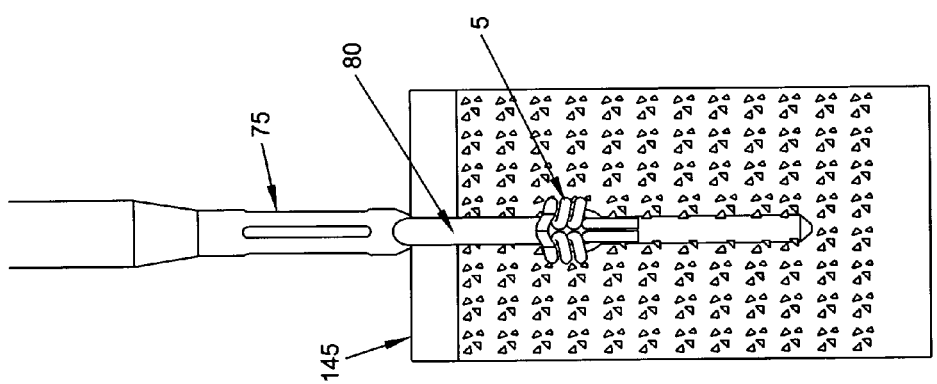
Figure 24:
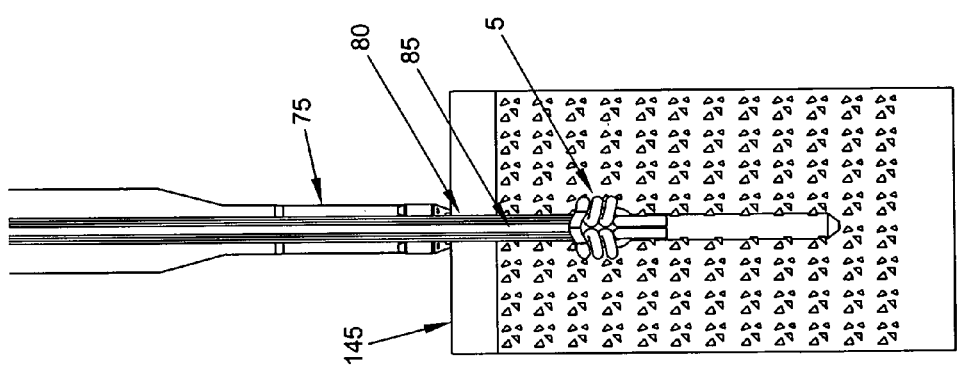
Figure 25:
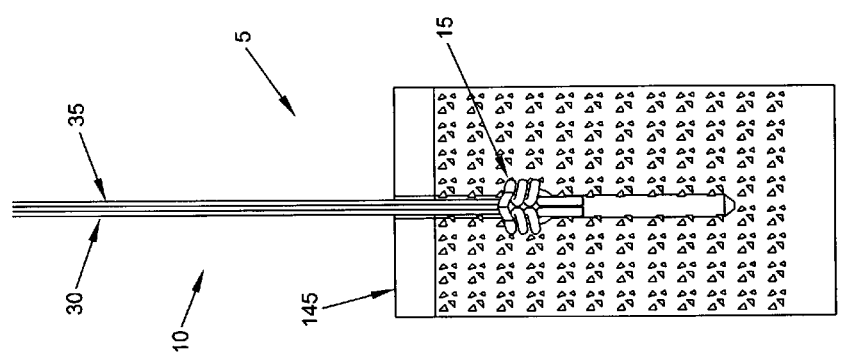
Figure 26:
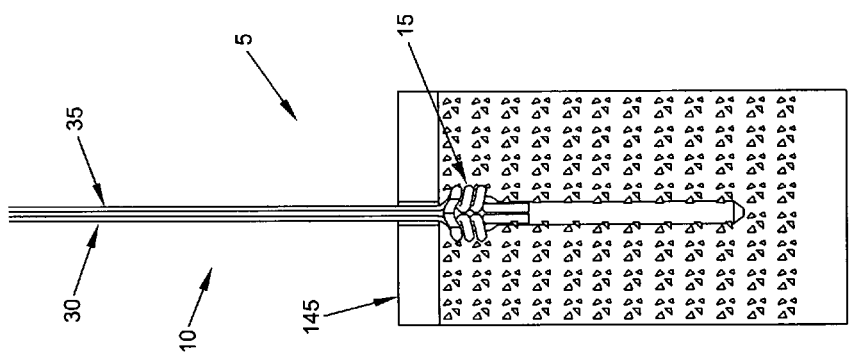
Figure 27:
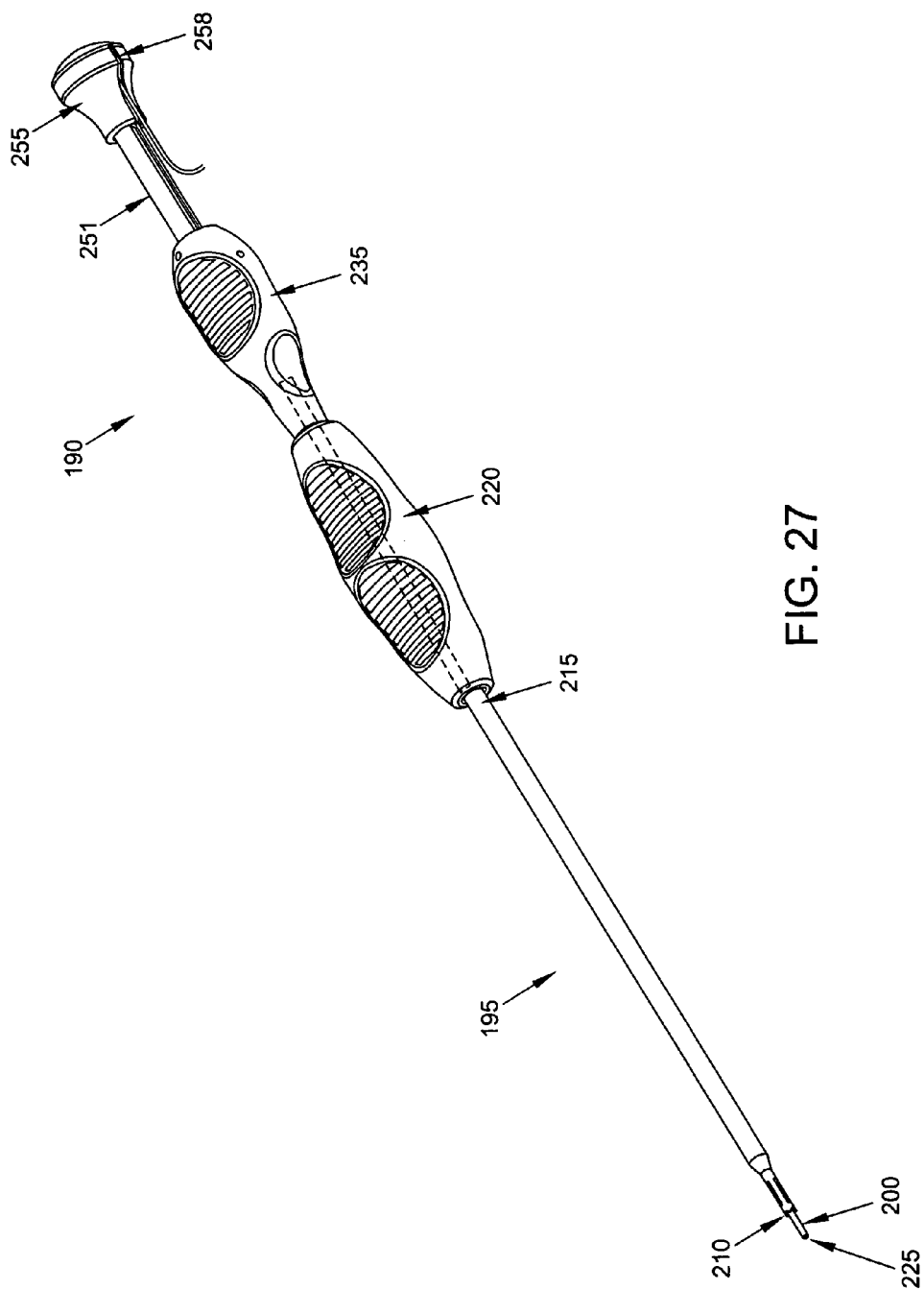
FIGS. 27-31 are schematic views showing another inserter assembly and associated cannulated drill guide assembly which may be used to deploy the novel suture assembly of FIG. 2 in a bone.
Figure 28:
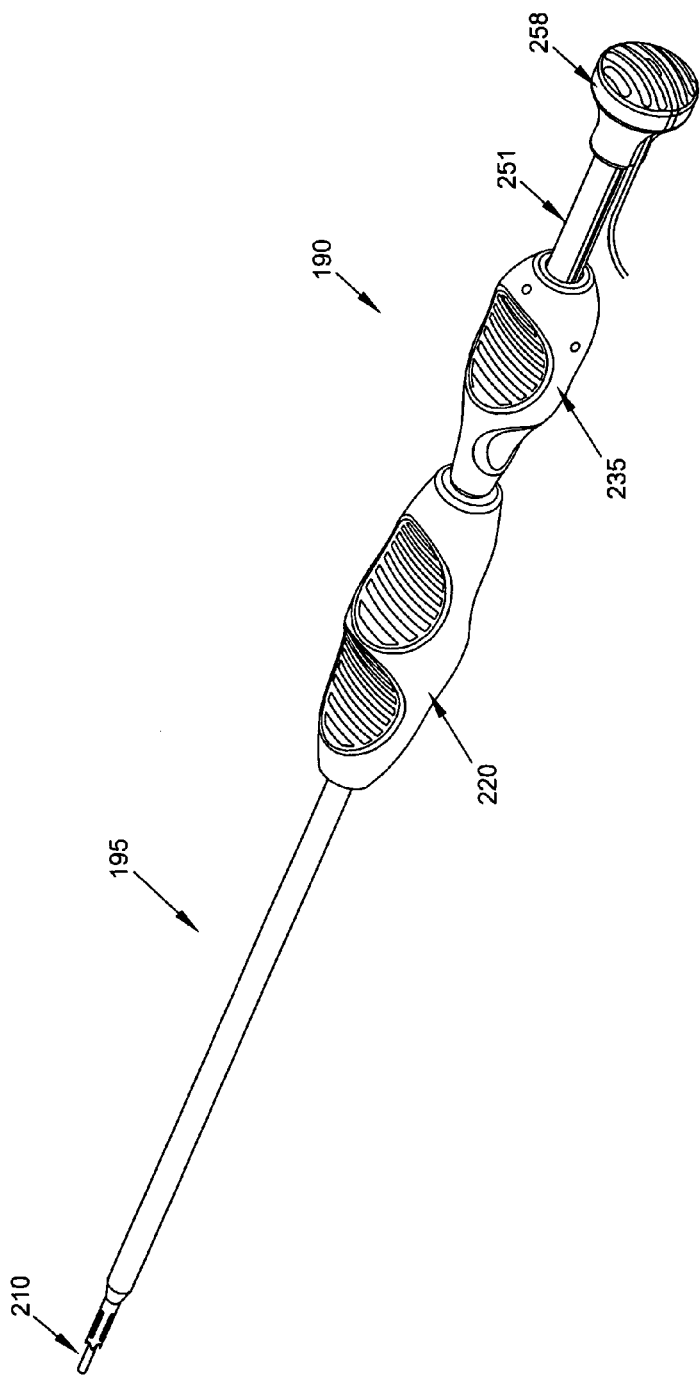
Figure 29:
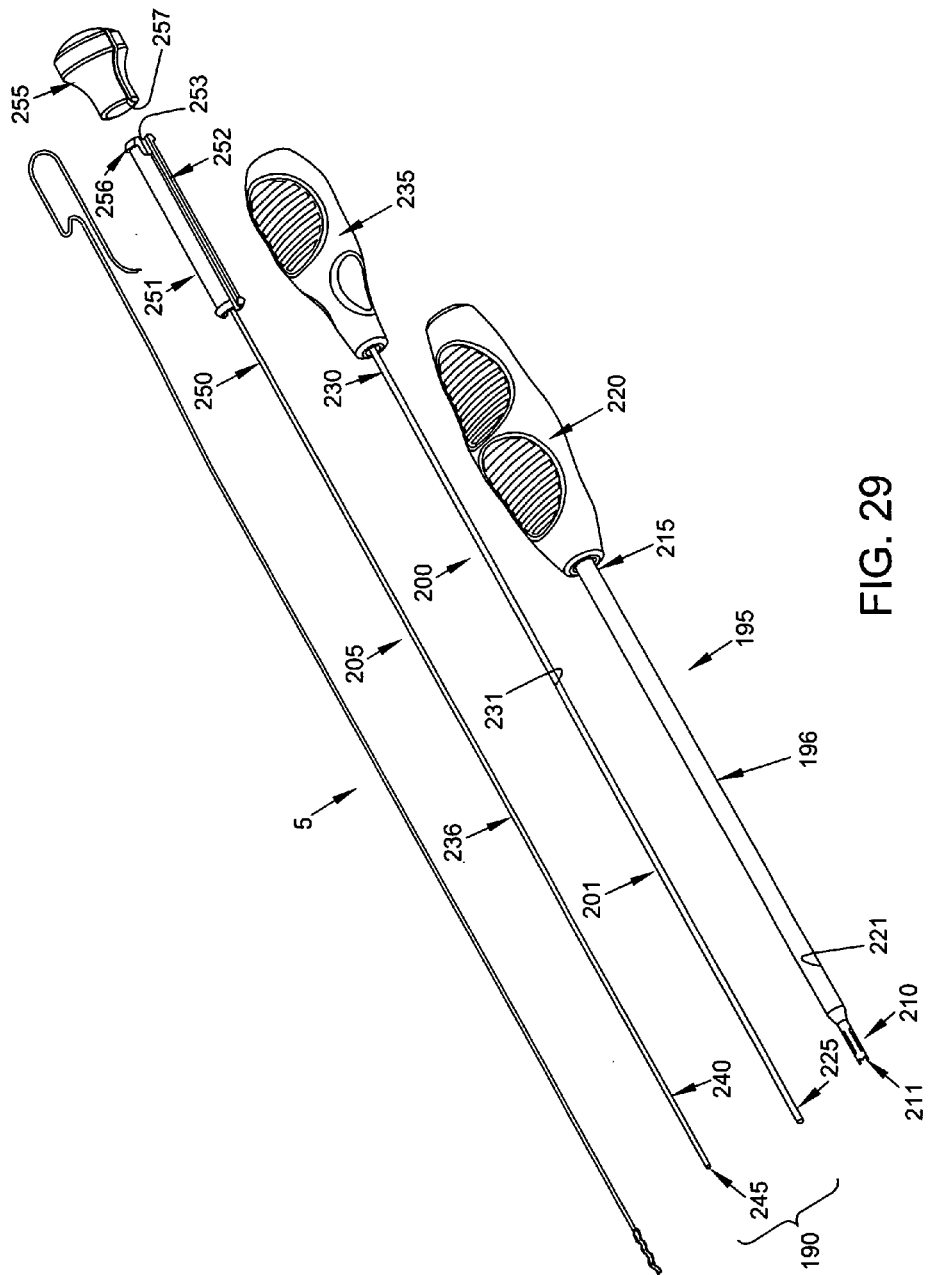
Figure 30:
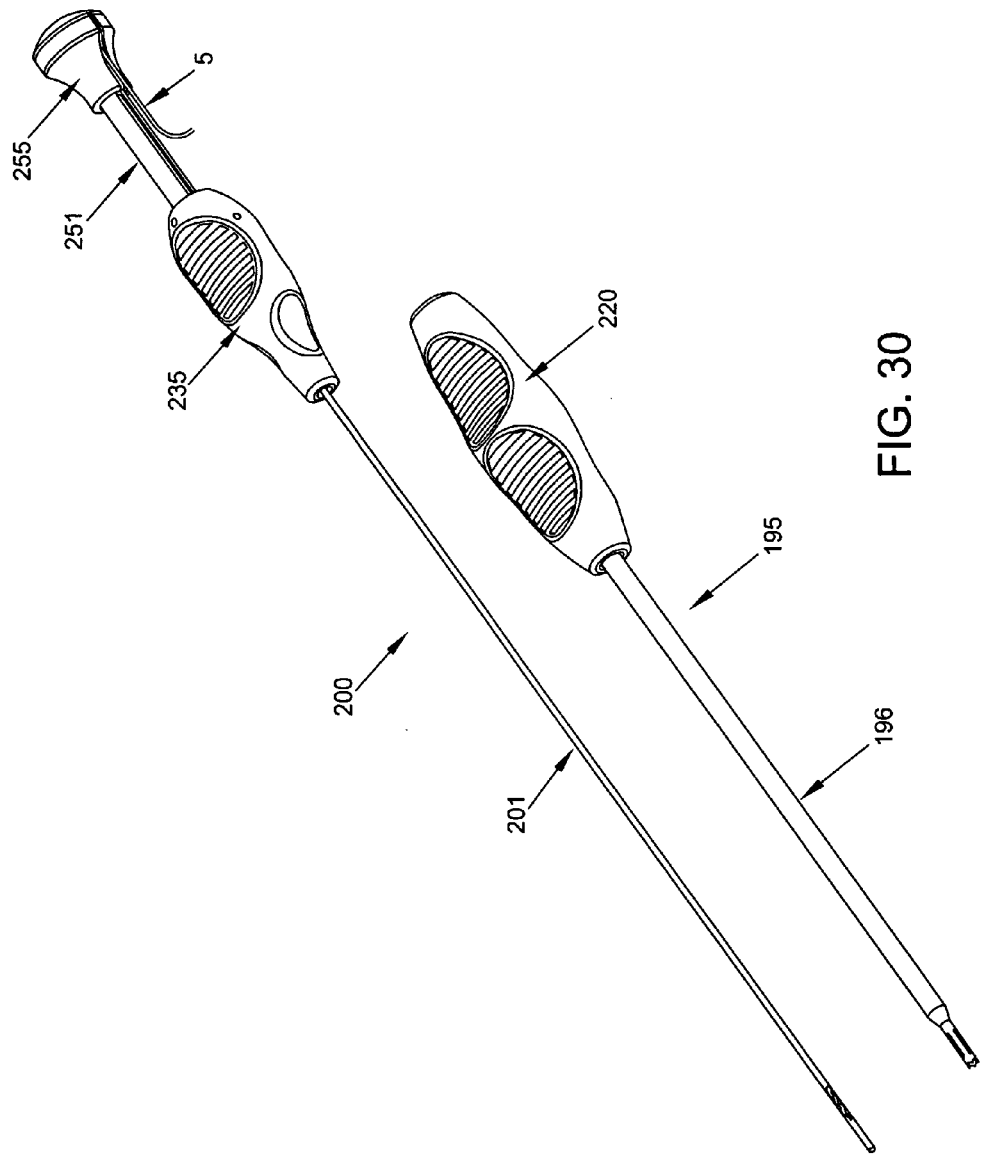
Figure 31:
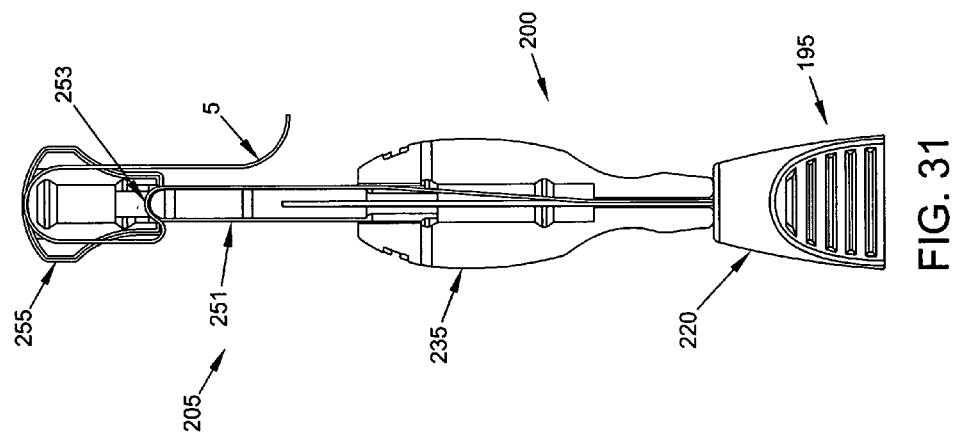
Figure 32:
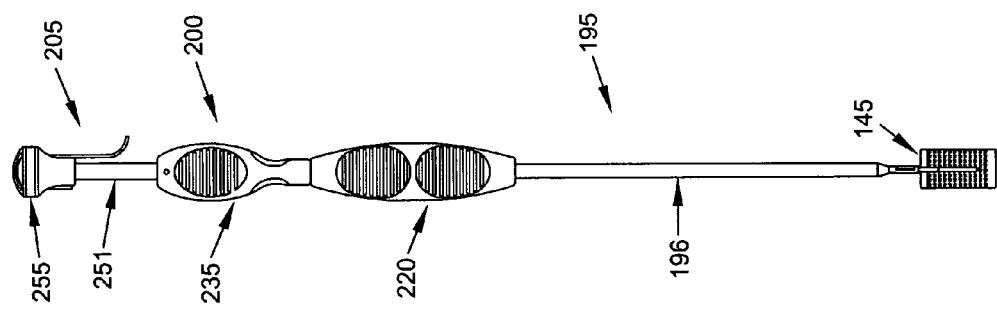
FIGS. 32-49 are schematic views showing the inserter assembly and associated cannulated drill guide assembly of FIGS. 27-31 deploying the novel suture assembly of FIG. 2 in a bone, with FIG. 49 showing the novel suture assembly released from the inserter assembly and in its longitudinally-contracted, radially-expanded second configuration so as to be secured to the bone.
Figure 33:
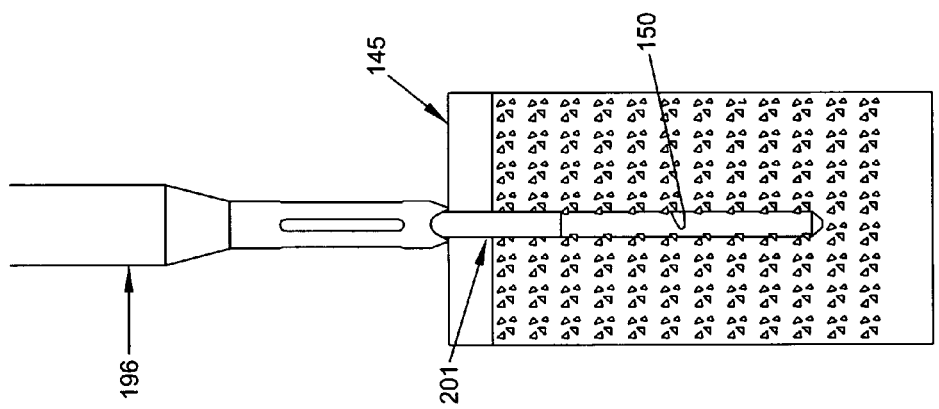
Figure 34:
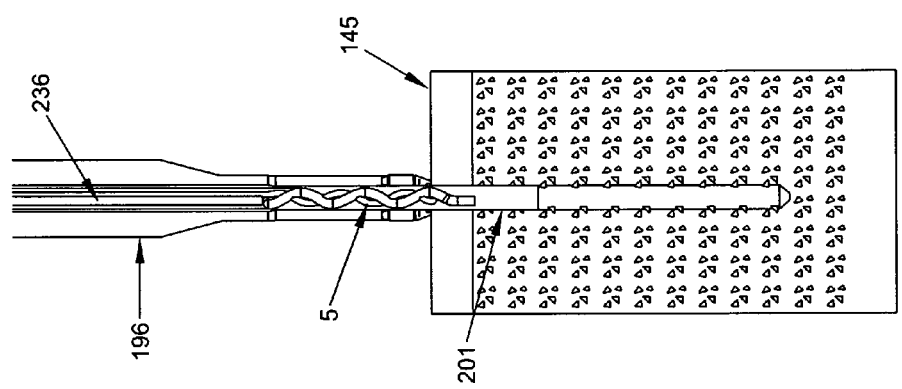
Figure 35:
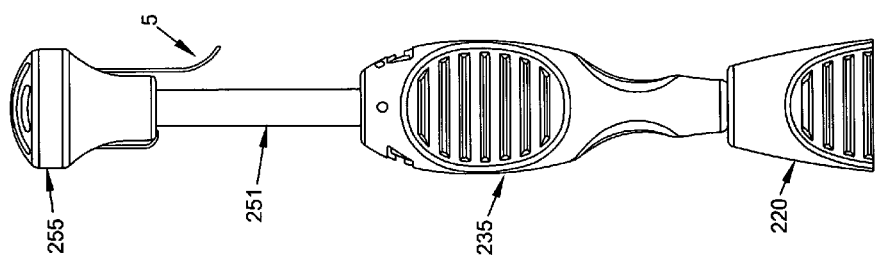
Figure 36:
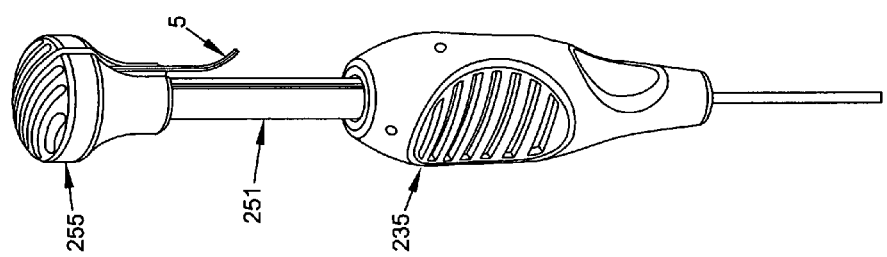
Figure 37:
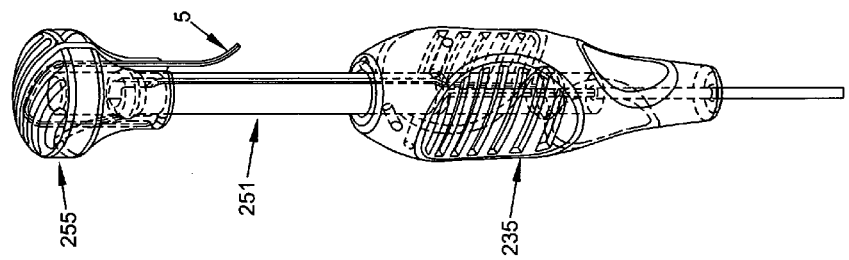
Figure 38:
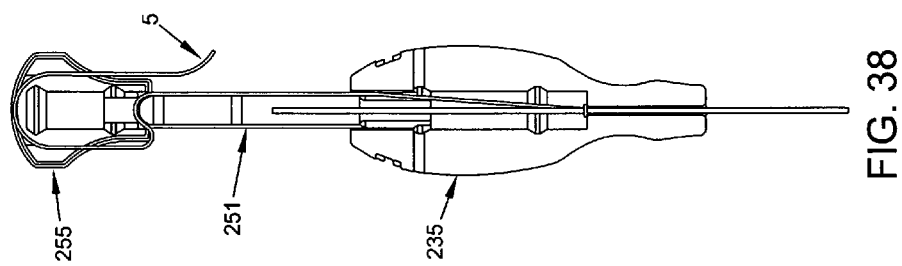
Figure 39:
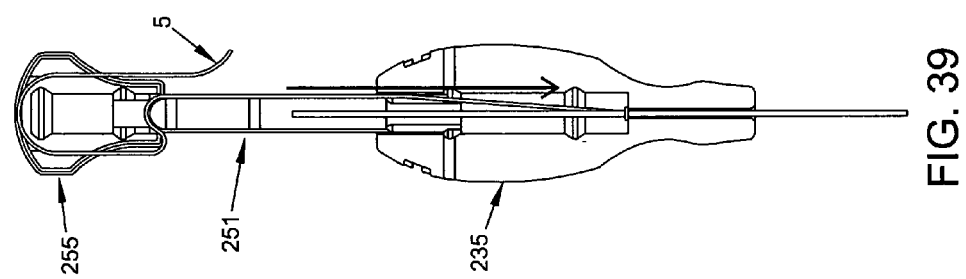
Figure 40:
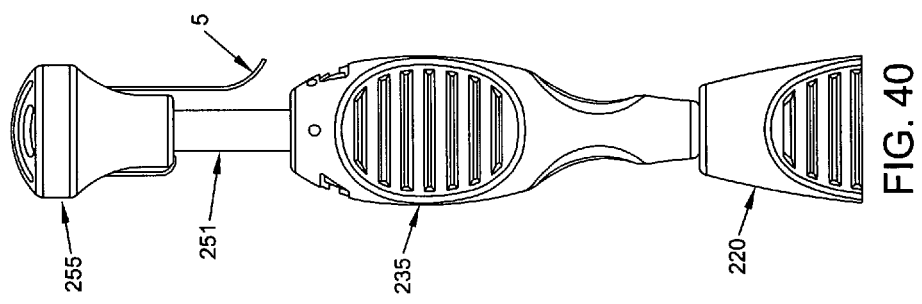

Next, push rod assembly 85 is advanced distally, against bridge 65 of second suture 15, so that novel suture assembly 5 is ejected from the distal end 110 of insertion tube assembly 80 (FIGS. 21 and 22).

Then, with push rod assembly 85 still in position against bridge 65 of second suture 15, first arm 30 and second arm 35 of first suture 10 are tensioned, thereby transforming novel suture assembly 5 from its longitudinally-extended, radially-contracted first configuration into its longitudinally-contracted, radially-expanded second configuration (FIGS. 23 and 24), whereby to expand novel suture assembly 5 laterally into the cancellous region 160 of bone 145.

At this point, inserter assembly 70 and cannulated drill guide assembly 75 are removed from the surgical site (FIG. 25), and first arm 30 and second arm 35 of first suture 10 are tensioned further so as to further laterally expand novel suture assembly 5 and cause the laterally-expanded novel suture assembly to seat against the underside of cortical layer 155 of bone 145 (FIG. 26), whereby to secure the novel suture assembly 5 within bone hole 150 (FIG. 26), with first arm 30 and second arm 35 of first suture 10 extending out of the bone hole.

Again, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6).

And again, the highly defined, appropriately shaped and consistently reproducible structure shown in FIGS. 5 and 6 is capable of carrying substantial loads without losing its defined shape when loads are applied to the first and second ends 20, 25 of first suture 10. As a result, when suture assembly 5 is inserted into a bone hole while in its longitudinally-expanded, radially contracted first configuration and is thereafter transformed into its longitudinally-contracted, radially-expanded second configuration, novel suture assembly 5 will provide an excellent suture anchor with high holding strength.

In one test configuration, a suture assembly 5 constructed as previously described was delivered into a 2 mm foam bone hole approximately 20-25 mm deep. The media was a 3 mm thick, 55-60 durometer foam bone layer over a 20 durometer foam bone block (Pacific Research Sawbones). The ultimate tensile strength of the suture assembly after insertion into foam bone was approximately 77 pounds. The ultimate tensile strength for another suture assembly after insertion into a 1.5 mm foam bone hole was approximately 50 pounds.

Thereafter, one or both of first arm 30 and second arm 35 of first suture 10 may be used to secure an object (e.g., soft tissue) to the bone. By way of example but not limitation, one or both of first arm 30 and second arm 35 may be passed through a piece of soft tissue (e.g., a ligament) and then tied together so as to secure the soft tissue to the bone.

Again, it should be appreciated that, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly. As a result, if at any time it should be desired to remove the novel suture assembly 5 from bone hole 150, first arm 30 of first suture 10, or second arm 35 of first suture 10, is simply pulled away from second suture 15, whereby to "undo" the suture assembly. Once first suture 10 has been pulled clear of the surgical site, second suture 15 may be extracted from bone hole 150 (e.g., with a narrow suture grasper) and removed from the surgical site.

Significantly, the novel suture assembly of the present invention can be sized in accordance with a wide range of anatomical applications. By way of example but not limitation, the novel suture assembly can be formed with relatively fine suture, and with a relatively small number of suture loops, so as to provide a relatively small structure for use with small and delicate anatomical structures. And a novel suture assembly of this type can be delivered through extremely small bone holes, e.g., on the order of 1 mm. Correspondingly, the novel suture assembly can be formed with relatively large suture, and with a relatively large number of suture loops, so as to provide a relatively large structure for use with robust anatomical structures. Significantly, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6). And, since the highly defined, appropriately shaped and consistently reproducible structure shown in FIGS. 5 and 6 is capable of carrying substantial loads without losing its defined shape when loads are applied to the first and second ends 20, 25 of first suture 10, the suture assembly 5 will provide an excellent suture anchor with high holding strength relative to its size (and relative to the size of the hole made in the host bone).

Furthermore, the novel suture assembly of the present invention can be used to attach objects to structures other than bone, e.g., the novel suture assembly can be used to attach skin to muscle.

Alternative Inserter Assembly for Deploying the Novel Suture Assembly

Looking next at FIGS. 27-31, there is shown an inserter assembly 190 and associated cannulated drill guide assembly 195 which may be used to deploy novel suture assembly 5 in bone. Inserter assembly 190 in turn comprises an insertion tube assembly 200 and a push rod assembly 205.

More particularly, drill guide assembly 195 generally comprises an elongated drill guide tube 196 having a distal end 210 carrying distal end prongs 211, and a proximal end 215 carrying a drill guide handle 220. A lumen 221 extends through elongated drill guide tube 196 and drill guide handle 220.

Figure 3:
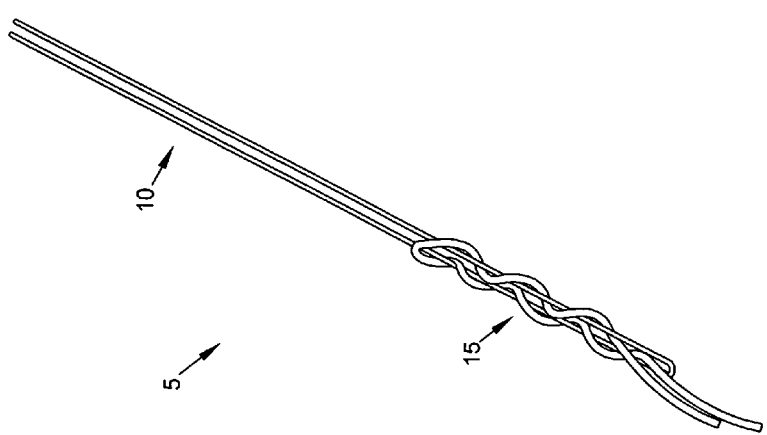
Figure 7:
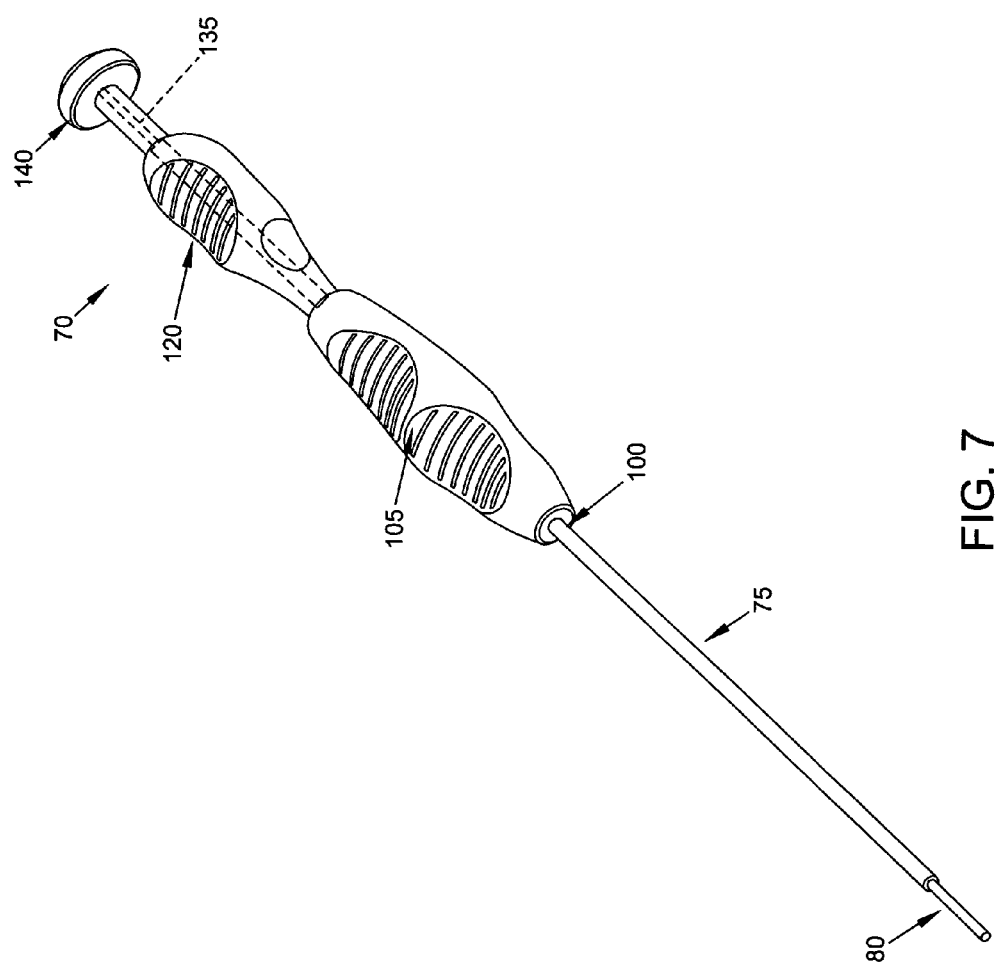
FIG. 7 is a schematic view showing an inserter assembly and associated cannulated drill guide assembly which may be used to deploy the novel suture assembly of FIG. 2 in a bone.
Figure 8:
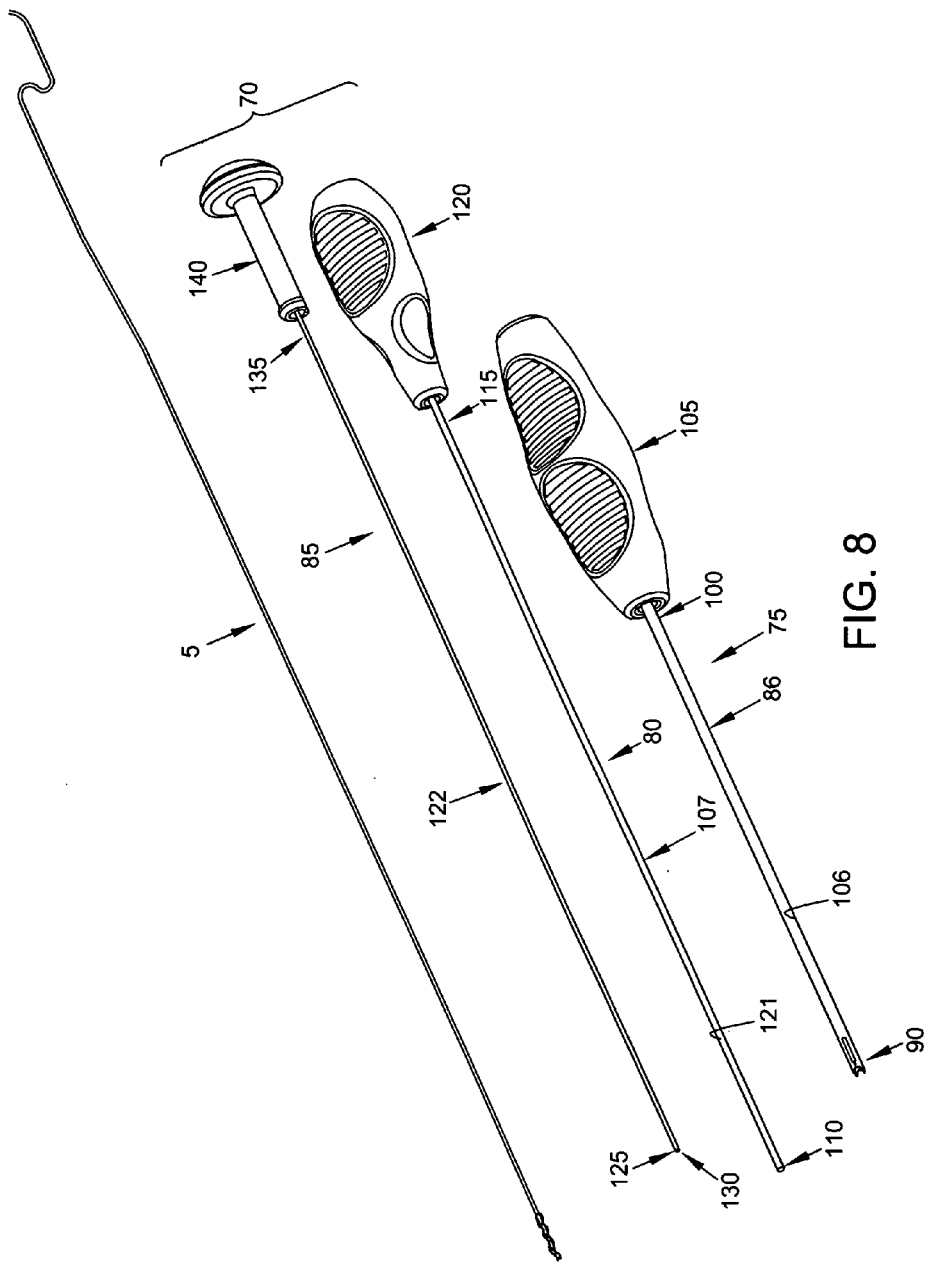
FIGS. 8-11 are schematic views showing various aspects of the inserter assembly and associated cannulated drill guide assembly of FIG. 7, and showing the novel suture assembly of FIG. 2 in its longitudinally-expanded, radially-contracted first configuration and loaded in the inserter assembly.
Figure 9:
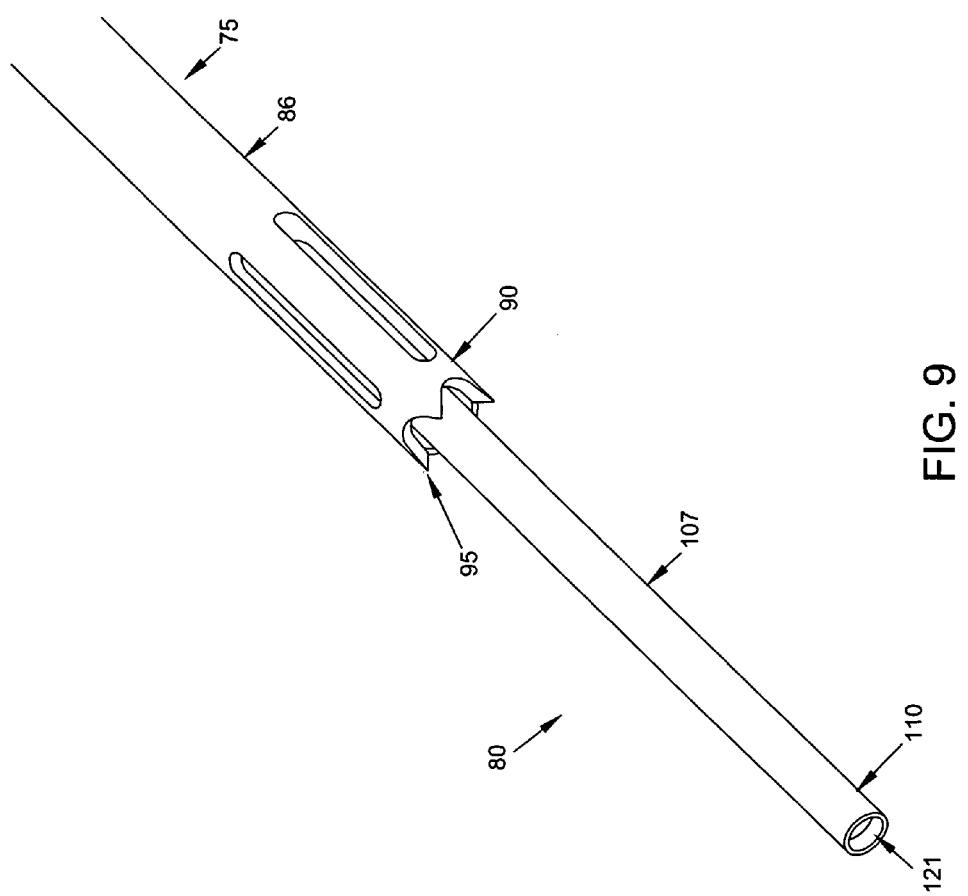
Figure 10:
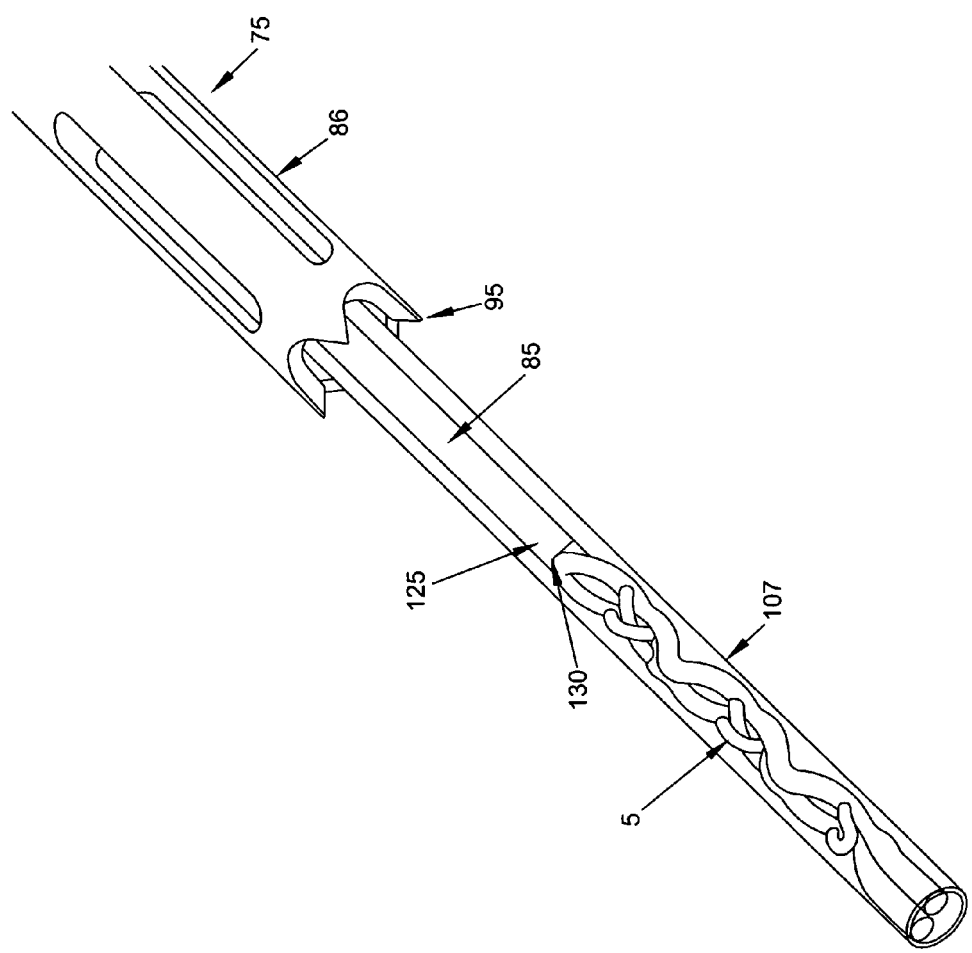
Figure 11:
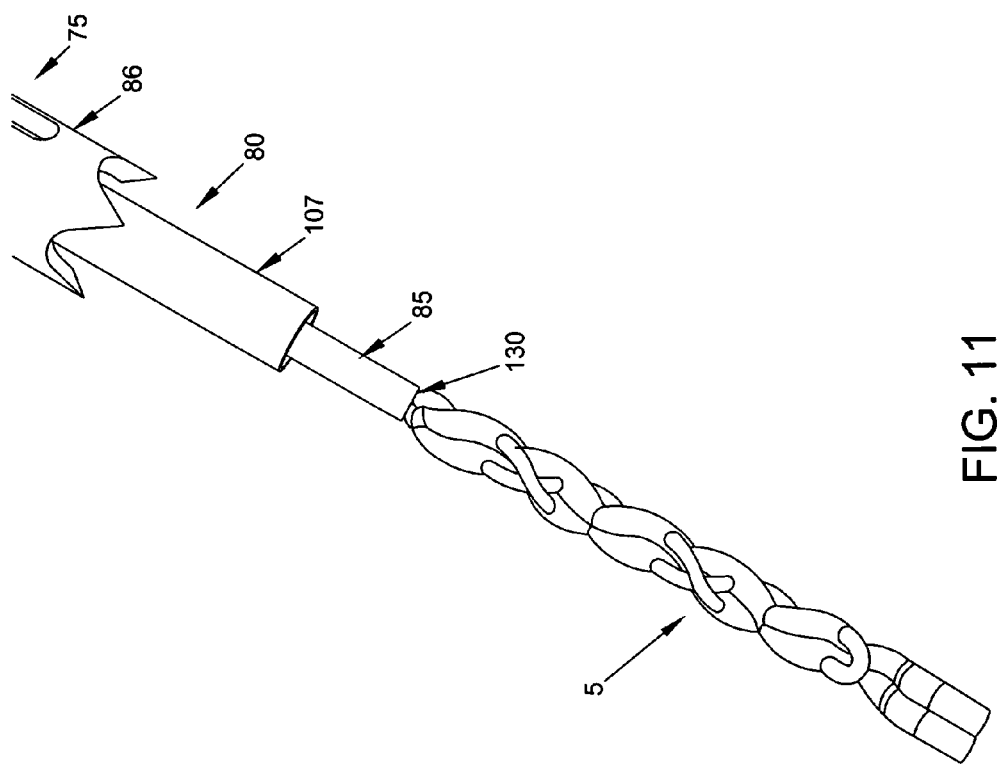
Figure 12:
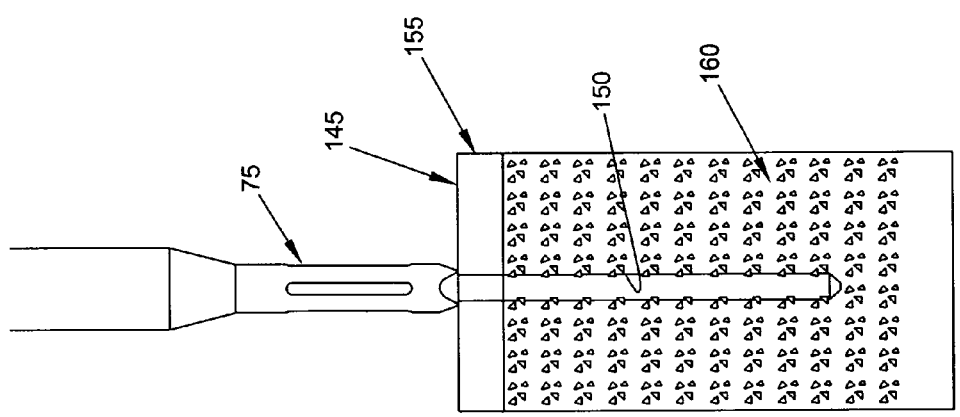
FIGS. 12-18 are schematic views showing one manner in which the inserter assembly and associated cannulated drill guide assembly of FIG. 7 can be used to deploy the novel suture assembly of FIG. 2 in a bone, with FIG. 18 showing the novel suture assembly released from the inserter assembly and in its longitudinally-contracted, radially-expanded second configuration so as to be secured to the bone.

Insertion tube assembly 200 generally comprises an elongated insertion tube 201 having a distal end 225 sized to receive novel suture assembly 5 (either loosely or, more preferably, tightly compressed) when the novel suture assembly is in its aforementioned longitudinally-extended, radially-contracted first configuration (FIGS. 3 and 4). Elongated insertion tube 201 of insertion tube assembly 200 also comprises a proximal end 230 carrying an insertion tube handle 235. A lumen 231 extends through elongated insertion tube 201 and insertion tube handle 235.

Push rod assembly 205 generally comprises a push rod 236 having a distal end 240 terminating in a distal end surface 245, and a proximal end 250 terminating in a push rod slide 251. Push rod slide 251 includes a suture slot 252 and suture saddle 253 which will hereinafter be discussed. A push rod handle 255 is slidably mounted on push rod slide 251 so that the push rod handle is longitudinally movable relative to the push rod slide. A detent mechanism comprising a radial projection 256 on push rod slide 251, which engages a counterpart element 257 on push rod handle 255, keeps push rod handle 255 in position on push rod slide 251 until a force of appropriate magnitude is applied to push rod handle 255, whereupon push rod handle 255 will move relative to push rod slide 251, as will hereinafter be discussed. Push rod handle 255 includes an undersized slot 258 for releasably binding a suture to the push rod handle.

Insertion tube assembly 200 is sized so that its elongated insertion tube 201 can be received within lumen 221 of cannulated drill guide assembly 195 such that, when cannulated drill guide assembly 195 is used to form a hole in a bone, the distal end of insertion tube assembly 200 can be delivered to that hole in a bone, as will hereinafter be discussed.

Push rod assembly 205 is sized so that its push rod 236 can be slidably received within lumen 231 of insertion tube assembly 200 such that, when novel suture assembly 5 is disposed within the distal end 225 of elongated insertion tube 201 of insertion tube assembly 200, advancement of push rod assembly 205 relative to insertion tube assembly 200 will cause novel suture assembly 5 to be ejected from distal end 225 of elongated insertion tube 201 of insertion tube assembly 200, as will hereinafter be discussed. Once novel suture assembly 5 has been ejected from distal end 225 of insertion tube 201 of insertion tube assembly 200, tensioning first arm 30 and second arm 35 of first suture 10, while push rod assembly 205 holds bridge 65 of second suture 15 from moving proximally, will cause novel suture assembly 5 to transform from its longitudinally-elongated, radially-contracted first configuration (FIGS. 3 and 4) into its longitudinally-contracted, radially-expanded second configuration (FIGS. 5 and 6). Such tensioning of first arm 30 and second arm 35 of first suture 10 is applied by moving push rod handle 255 longitudinally along push rod slide 251 (i.e., by applying a force of appropriate magnitude to the aforementioned detent mechanism), as will hereinafter be discussed.

Insertion tube assembly 200 is also sized so that its lumen 231 will accommodate first and second arms 30, 35 of first suture 10 alongside push rod 236 of push rod assembly 205 when push rod 236 is disposed in lumen 231 of insertion tube assembly 200.

Novel suture assembly 5 is intended to be disposed within the distal end of insertion tube assembly 200, distal to push rod assembly 205, with first arm 30 and second arm 35 of first suture 10 extending up lumen 231 of insertion tube assembly 200 (and alongside push rod 236 of push rod assembly 205), along suture slot 252 of push rod slide 251, around suture saddle 253 of push rod slide 251 and then into undersized slot 258 of push rod handle 255, whereby to releasably bind first and second arms 30, 35 of first suture 10 to push rod handle 255. Preferably novel suture assembly 5 is tightly compressed within the distal end of insertion tube assembly 200, so as to provide the largest possible differential between the diameter of the radially-elongated, radially-contracted first configuration (FIGS. 3 and 4) and the longitudinally-contracted, radially-expanded second configuration (FIGS. 5 and 6), whereby to minimize the size of the bone hole and thereby increase holding power in the bone. In this respect it should be appreciated that by winding first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively, it is possible for the first and second sutures 10, 15 to "self-accommodate" within the interior of insertion tube assembly 200, thereby permitting maximum compression of the novel suture assembly within the insertion tube. Furthermore, by leaving first end 45 and second end 50 of second suture 15 free (i.e., unconnected) relative to one another, the first and second sutures 10, 15 can further self-accommodate within the interior of insertion tube assembly 200, thereby permitting maximum compression of the novel suture assembly within the insertion tube assembly. Thus it will be appreciated that, by forming novel suture assembly 5 in the specific manner discussed above, the suture assembly is capable of self-accommodating itself into the smallest possible diameter within the insertion tube assembly, thereby permitting maximum compression of the novel suture assembly within the insertion tube assembly, and hence permitting use of a smaller bone hole and thus providing maximum holding power within the bone.

Significantly, push rod handle 255 is slidably mounted to push rod slide 251 using a detent mechanism, and the first arm 30 and second arm 35 of first suture 10 are releasably secured to push rod handle 255 after first passing over suture saddle 253 of push rod slide 251, such that (i) by initially applying a force to push rod handle 255 which is below the trigger magnitude of the aforementioned detent mechanism, push rod handle 255 will initially cause push rod assembly 205 to be moved distally relative to insertion tube assembly 200, whereby to eject suture assembly 205 from insertion tube assembly 200, and (ii) by thereafter applying a force to push rod handle 255 which is above the trigger magnitude of the aforementioned detent mechanism, push rod handle 255 will thereafter move relative to push rod slide 251, whereby to cause tension to be applied to first arm 30 and second arm 35 of first suture 10 without causing further distal motion of push rod 236.

Thus, with this form of the invention, once novel suture assembly 5 has been ejected from distal end 225 of insertion tube assembly 200, first arm 30 and second arm 35 of first suture 10 are automatically tensioned, while push rod assembly 205 holds bridge 65 of second suture 15 from moving proximally, whereby to cause novel suture assembly 5 to transform from its longitudinally-elongated, radially-contracted first configuration (FIGS. 3 and 4) into its longitudinally-contracted, radially-expanded second configuration (FIGS. 5 and 6).

In essence, in this form of the invention, progressive distal movement of push rod handle 255 causes novel suture assembly 5 to first be ejected into a bone hole and then transformed from its longitudinally-elongated, radially-contracted first configuration into its longitudinally-contracted, radially-expanded second configuration.

Using the Alternative Inserter Assembly for Deploying the Novel Suture Assembly, in Order to Secure an Object to Bone The alternative inserter assembly 190 shown in FIGS. 27-31 and its associated cannulated drill guide assembly 195 may be used to deploy novel suture assembly 5 in bone, in order to secure an object to bone.

Thus, in another preferred form of the present invention, and looking now at FIGS. 32-49, the distal end of cannulated drill guide assembly 195 is first placed against the surface of bone 145, then a bone drill (not shown) of the sort well known in the art is advanced through lumen 221 of the cannulated drill guide assembly and into the bone so that a bone hole 150 of appropriate size (diameter and depth) is formed in the bone, then the bone drill is removed from lumen 221 of cannulated drill guide assembly 195 while leaving the cannulated drill guide assembly in position against bone 145, and then the distal end 225 of insertion tube assembly 200, carrying novel repair contruct 5 therein, is advanced through cannulated drill guide assembly 195 and into bone hole 150 formed in bone 145 (FIGS. 32-38). It will be appreciated that push rod 236 of push rod assembly 205 is already disposed within lumen 231 of insertion tube assembly 200 as this occurs, with distal end 240 of push rod assembly 205 sitting against bridge 65 of second suture 15.

Figure 41:
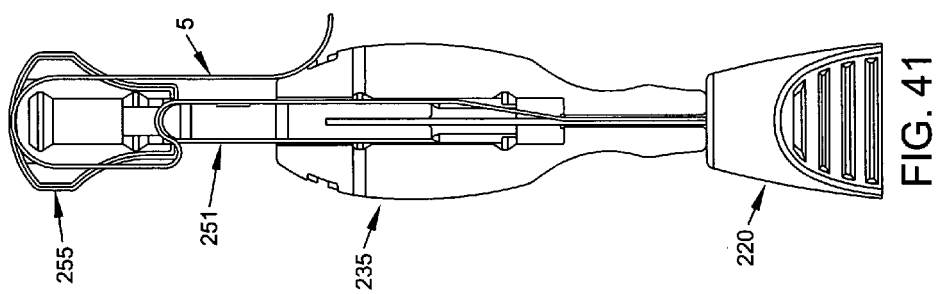
Figure 42:
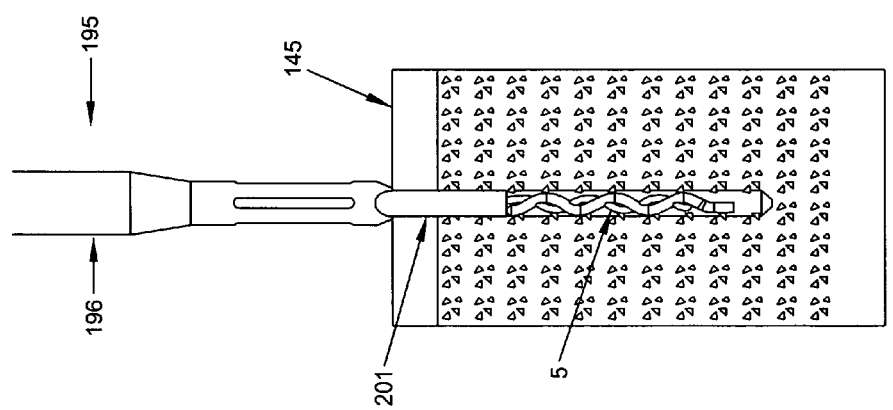
Figure 43:
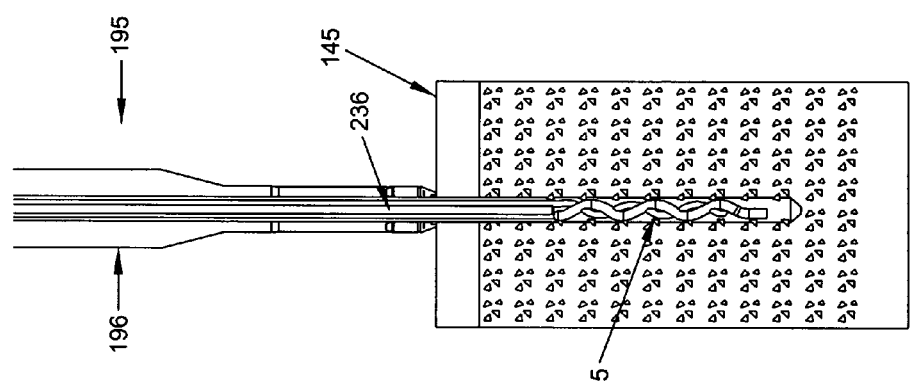
Figure 44:
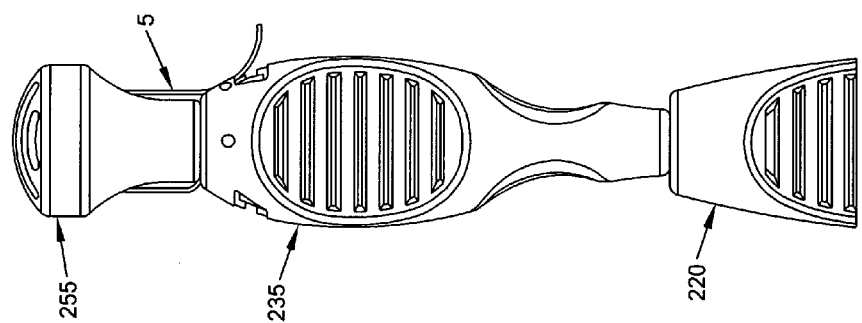
Figure 45:
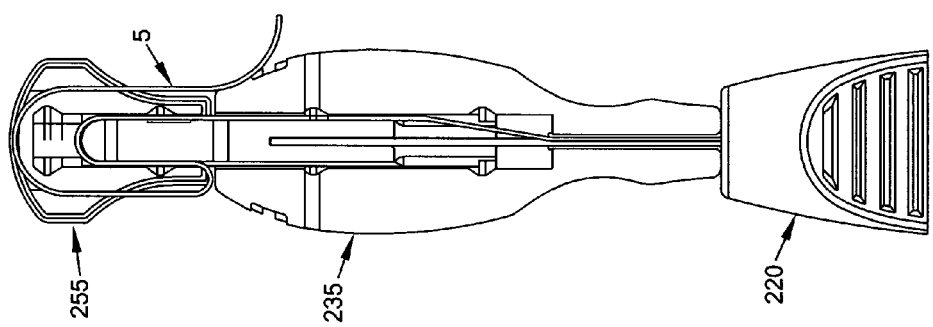
Figure 46:
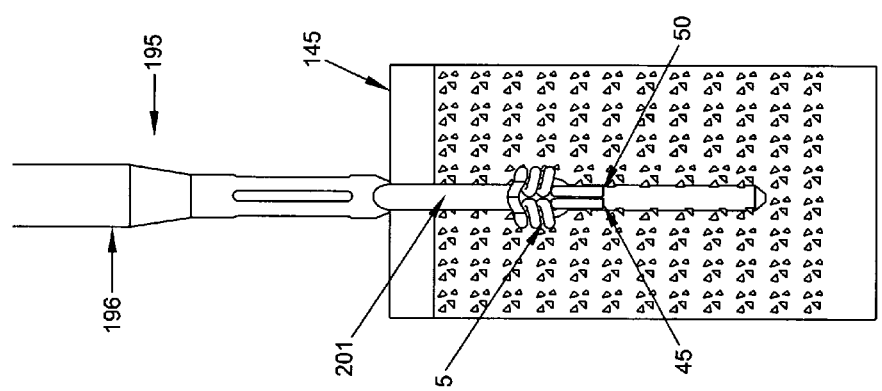
Figure 47:
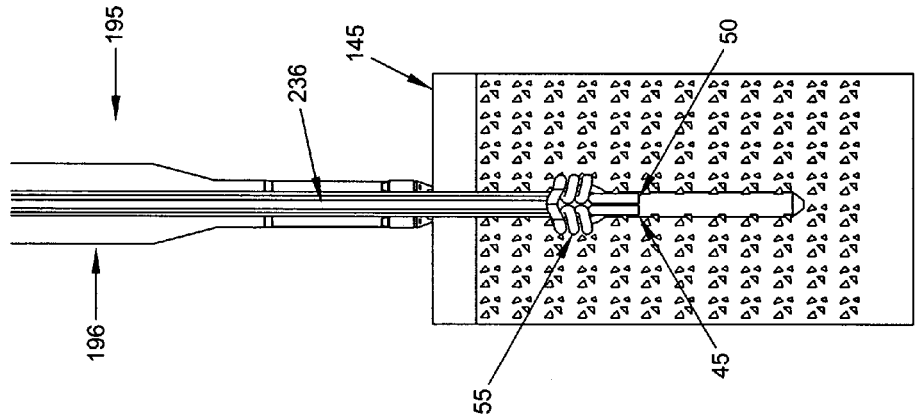
Figure 48:
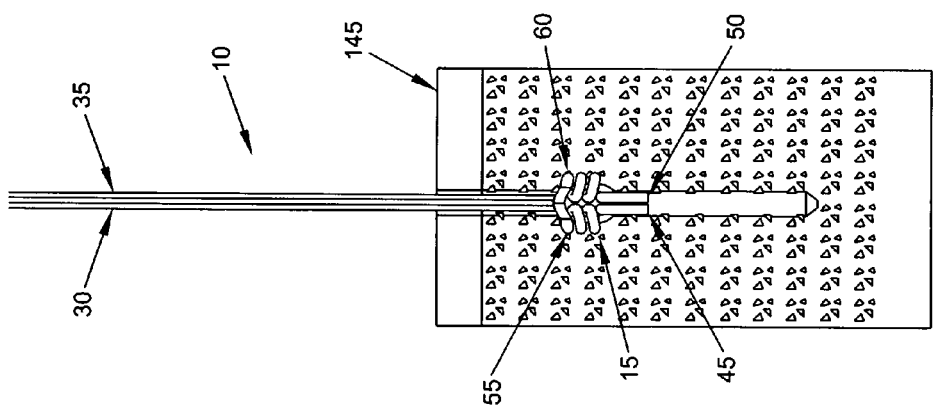
Figure 49:
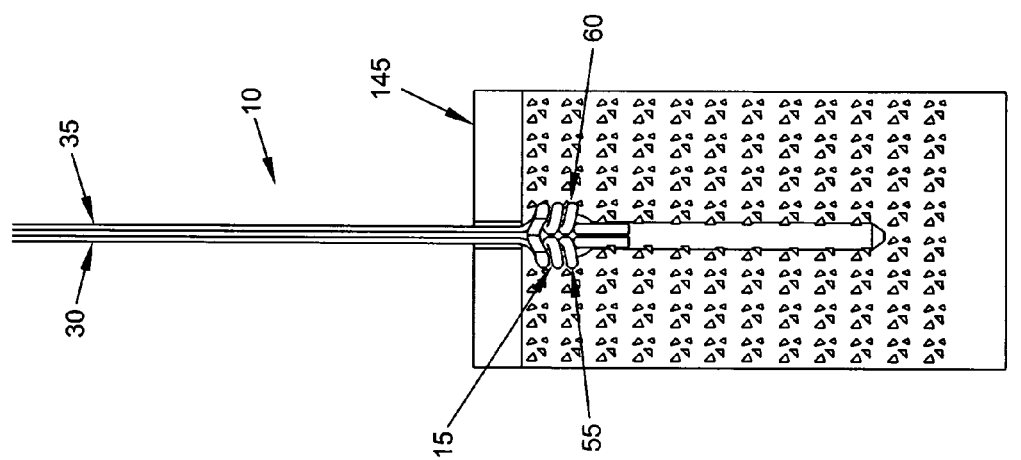

Next, push rod assembly 205 is advanced distally, against bridge 65 of second suture 15, so that novel suture assembly 5 is ejected from the distal end 225 of insertion tube assembly 200 (FIGS. 39-43). This is done by pressing push rod handle 255 distally so that push rod assembly 205 advances distally relative to insertion tube 200. As this occurs, push rod handle 255 remains fixed in position on push rod slide 251 due to the detent mechanism of radial projection 256 on push rod slide 251 and counterpart element 257 on push rod handle 255. Push rod assembly 205 advances distally until push rod slide 251 bottoms out in its seat on insertion tube handle 235 (FIG. 41).

Then, with push rod assembly 205 still in position against bridge 65 of second suture 15, first arm 30 and second arm 35 of first suture 10 are tensioned, thereby transforming novel suture assembly 5 from its longitudinally-extended, radially-contracted first configuration into its longitudinally-contracted, radially-expanded second configuration (FIGS. 44-47), whereby to expand novel suture assembly 5 laterally into the cancellous region 160 of bone 145. This is done by pressing push rod handle 255 further distally so that push rod handle 255 overcomes the aforementioned detent mechanism with push rod slide 251, thereby causing push rod handle 255 to move distally along push rod slide 251, relative to insertion tube assembly 200 and push rod assembly 205. As this occurs, the first and second arms 30, 35 of first suture 10 are tensioned, due to the increasing length of the suture path created around suture saddle 253.

At this point, first and second arms 30, 35 of first suture 10 are released from inserter assembly 190 (e.g., by dismounting the suture arms from undersized slot 258 of push rod handle 255), inserter assembly 190 is removed from the surgical site (FIG. 48), and then first arm 30 and second arm 35 of first suture 10 are tensioned further so as to further laterally expand novel suture assembly 5 and cause the laterally-expanded novel suture assembly to seat against the underside of cortical layer 155 of bone 145 (FIG. 49), whereby to secure the novel suture assembly 5 within bone hole 150, with first arm 30 and second arm 35 of first suture 10 extending out of the bone hole.

Significantly, by forming novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6).

And significantly, the highly defined, appropriately shaped and consistently reproducible structure shown in FIGS. 5 and 6 is capable of carrying substantial loads without losing its defined shape when loads are applied to the first and second ends 20, 25 of first suture 10. As a result, when suture assembly 5 is inserted into a bone hole while in its longitudinally-expanded, radially-contracted first configuration and is thereafter transformed into its longitudinally-contracted, radially-expanded second configuration, novel suture assembly 5 will provide an excellent suture anchor with high holding strength.

Thereafter, one or both of first arm 30 and second arm 35 of first suture 10 may be used to secure an object (e.g., soft tissue) to the bone. By way of example but not limitation, one or both of first arm 30 and second arm 35 may be passed through a piece of soft tissue (e.g., a ligament) and then tied together so as to secure the soft tissue to bone.

Again, it should be appreciated that, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly. As a result, if at any time it should be desired to remove the novel suture assembly 5 from bone hole 150, first arm 30 of first suture 10, or second arm 35 of first suture 10, is simply pulled away from second suture 15, whereby to "undo" the suture assembly. Once first suture 10 has been pulled clear of the surgical site, second suture 15 may be extracted from bone hole 150 (e.g., with a narrow suture grasper) and removed from the surgical site.

Significantly, since the novel suture assembly 5 is a relatively flexible structure while it is in its aforementioned longitudinally-elongated, radially-contracted first configuration, it is capable of conforming to some extent to the geometry of the bone hole in which it is received as it is ejected from insertion tube assembly 200 and before it is transformed into its longitudinally-contracted, radially-expanded second configuration. As a result, the novel suture assembly 5 can be deployed in relatively shallow bone holes, since it is relatively pliable when it is in its longitudinally-elongated, injection-state configuration and before it is transformed into its longitudinally-contracted, anchoring-state configuration.

Alternative Forms of the Novel Suture Assembly

FIG. 2 shows the preferred manner of forming novel suture assembly 5.

Figure 50:
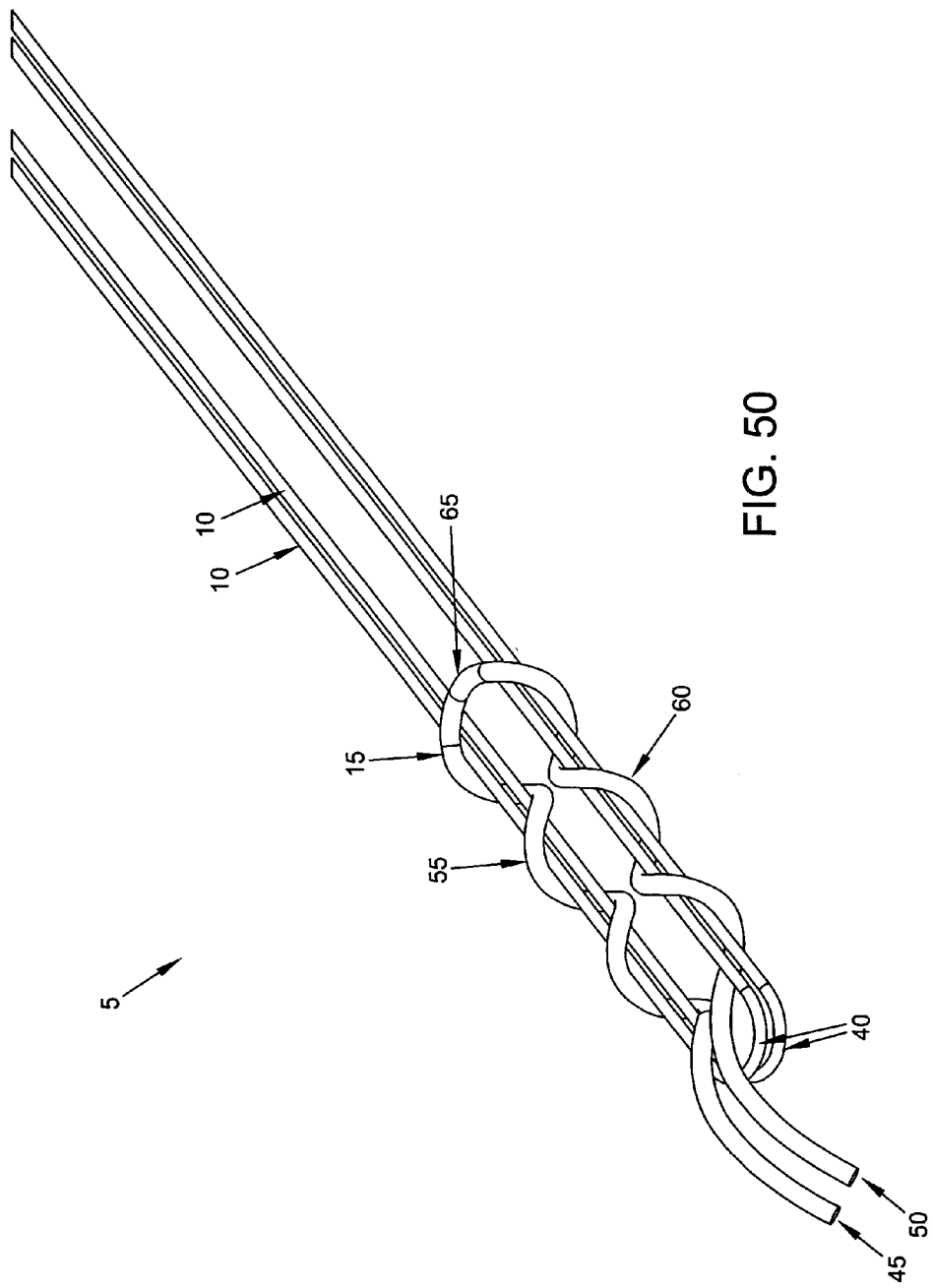
FIGS. 50-54 are schematic views showing alternative forms of the novel suture assembly of FIG. 2.

FIG. 50 shows an alternative manner of forming novel suture assembly 5. In this form of the invention, suture assembly 5 is substantially the same as the suture assembly shown in FIG. 2, except that two first sutures 10, disposed in a parallel arrangement, are provided. This construction can be highly advantageous in some situations since it provides four strands of suture emerging from the bone hole.

Figure 51:
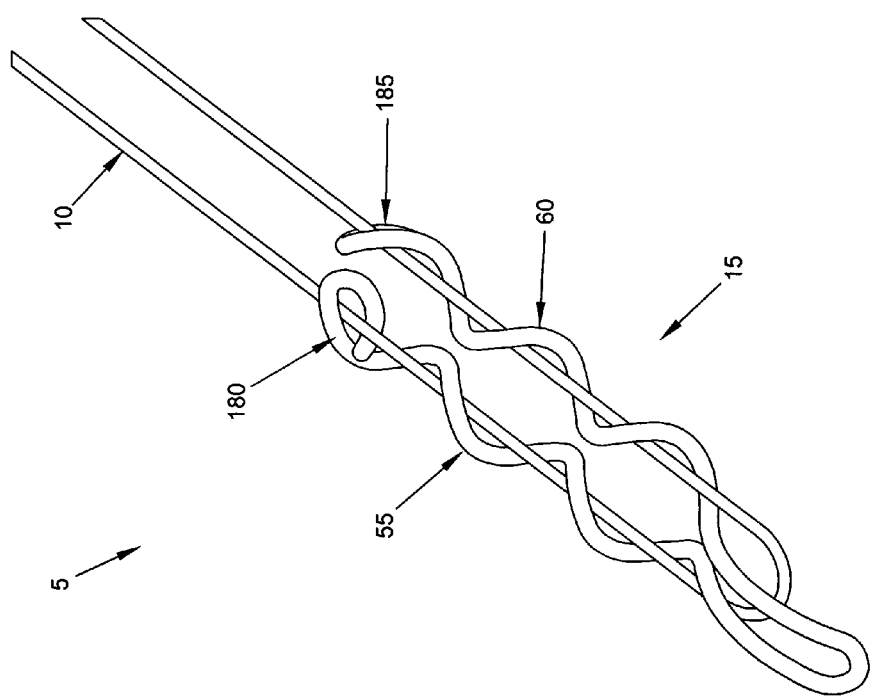

FIG. 51 shows another manner of forming the novel suture construct 5. In this form of the invention, second suture 15 has an eyelet 180 formed on the end of first arm 55 and an eyelet 185 formed on the end of second arm 60. First arm 55 of second suture 15 is wrapped (e.g., three times) around first arm 30 of first suture 10, with first arm 30 of first suture 10 passing through eyelet 180 of second suture 15, and second arm 60 of second suture 15 is wrapped (e.g., three times) around second arm 35 of first suture 10, with second arm 35 of first suture 10 passing through eyelet 185 of second suture 15. Again, first arm 55 of second suture 15 is wrapped in the opposite direction from second arm 60 of second suture 15. In this form of the invention, bridge 65 of second suture 15 may be positioned close to, and extend substantially parallel to, bridge 40 of first suture 10. While this form of the invention may permit enhanced compression of the novel suture assembly within the insertion tube, it is generally not preferred since it presents separate eyelets 180, 185 to the distal end of the push rod assembly, rather than an integrated bridge 65, and can be more difficult to reliably engage with the distal end of the push rod assembly.

Figure 52:
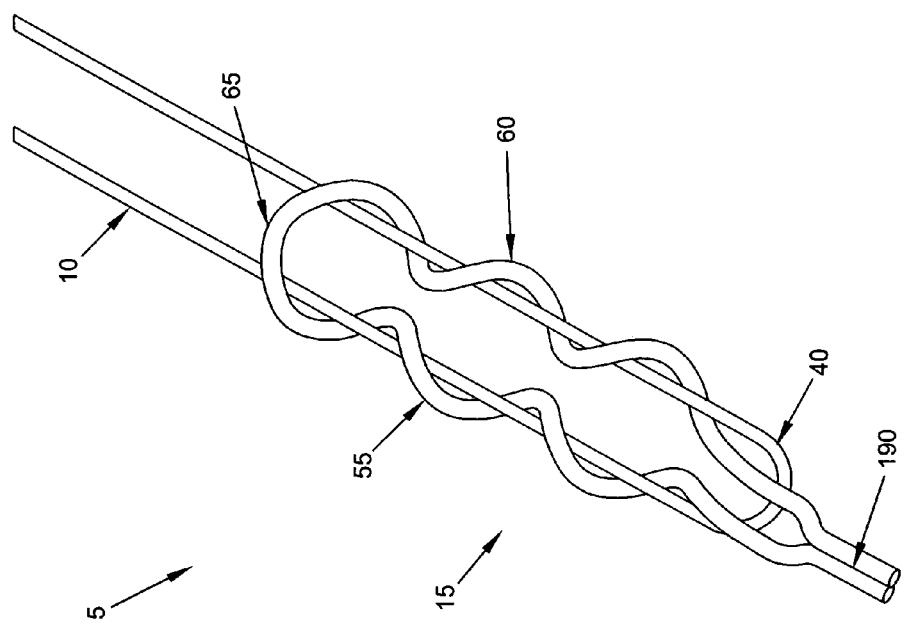
Figure 53:
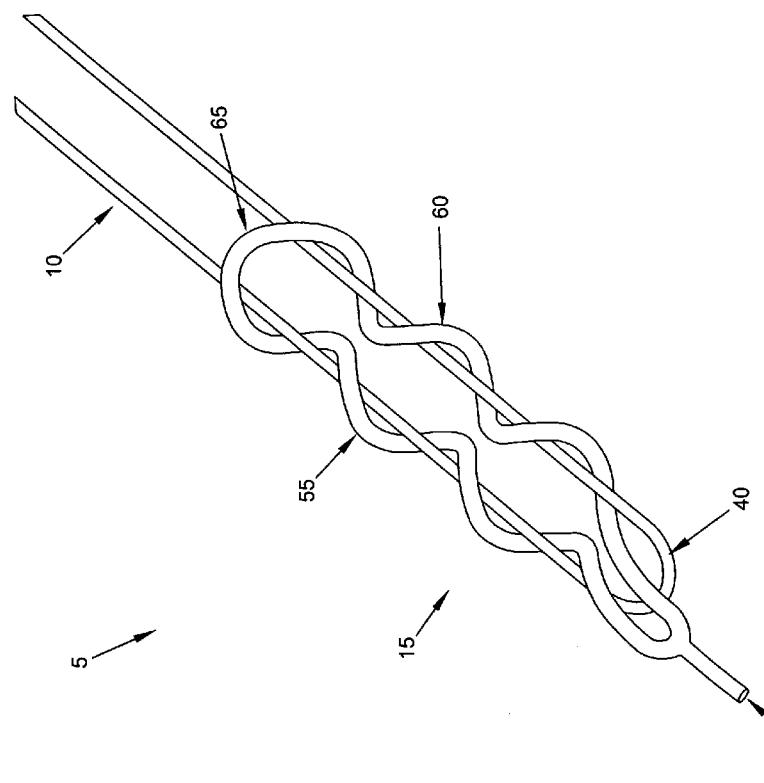
Figure 54:
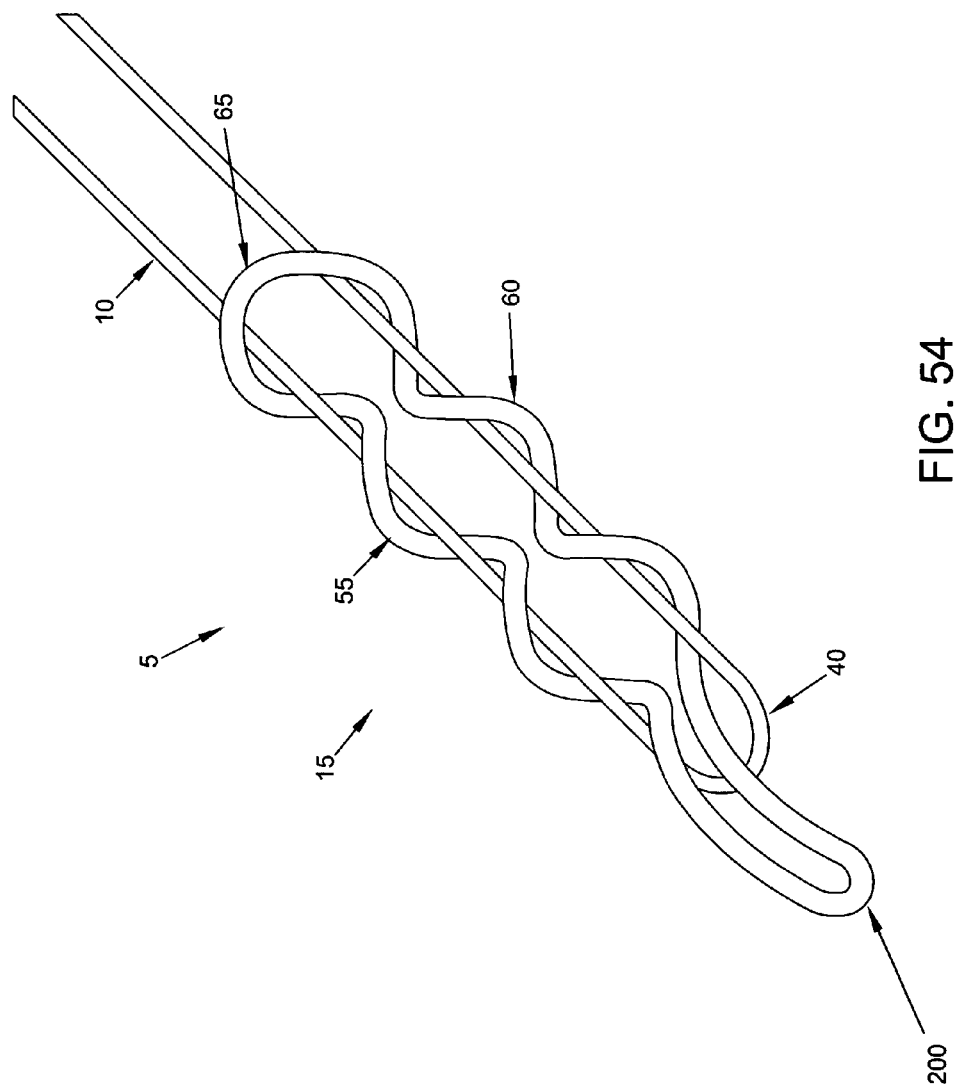

Additional configurations are shown in FIGS. 52-54. More particularly, the suture construct shown in FIG. 52 is substantially the same as the suture assembly shown in FIG. 2, except that the first and second ends 45, 50 of second suture 15 are joined together at 190 such that the second suture forms a substantially closed loop. Various means may be used to join together the first and second ends of second suture 15, e.g., simply tying the ends into a knot (not shown); gluing or thermal welding, the use of a mechanical means or device such as a pledget that joins the ends together (not shown), etc. Additionally, one end of second suture 15 can be inserted through the body of the other end so as to form a single strand 195 (FIG. 53). Furthermore, second suture 15 can be manufactured as a closed loop, i.e., so as to provide a distal bridge 200 (FIG. 54).

The constructions shown in FIGS. 52-54 can work adequately in some situations, e.g., where a larger bone hole size is acceptable and lower holding strengths can be tolerated. However, it must be emphasized that the suture assemblies shown in FIGS. 52-54 are not equivalent to the suture assembly shown in FIGS. 1-6 in either form or function. More particularly, with the suture assemblies shown in FIGS. 52-54, second suture 15 effectively forms a substantially closed loop, whereas with the suture assembly of FIGS. 1-6, the second suture 15 provides two free ends. The provision of two free ends with the suture assembly of FIGS. 1-6 is a significant advantage over the suture assemblies shown in FIGS. 52-54, inasmuch as it permits the suture assembly to self-accommodate within the insertion tube, thereby permitting substantially better compression of the suture assembly within the insertion tube. Again, this is significant, since better compression of the suture assembly within the insertion tube permits the use of a smaller bone hole, a smaller insertion tube and provides significantly better binding to the bone.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A suture assembly comprising:
a first suture having a generally U-shaped configuration comprising a first arm, a second arm and a first bridge connecting the first arm of the first suture to the second arm of the first suture;
a second suture comprising a first arm, a second arm and a second bridge connecting the first arm of the second suture to the second arm of the second suture;
the first arm of the second suture being wound helically around the first arm of the first suture in a single first direction, and the second arm of the second suture being wound helically around the second arm of the first suture in a single second, opposite direction;
wherein the first arm of the second suture is wound three times around the first arm of the first suture and the second arm of the second suture is wound three times around the second arm of the first suture;
the suture assembly being capable of assuming (i) a longitudinally-extended, radially-contracted first configuration, and (ii) a longitudinally-contracted, radially-expanded second configuration.

2. A suture assembly according to claim 1 wherein the suture assembly is transformed from its longitudinally-extended, radially-contracted first configuration to its longitudinally-contracted, radially-expanded second configuration by moving the wound portions of the second suture along the first and second arms of the first suture.

3. A suture assembly according to claim 1 wherein the wound portions of the second suture are in a longitudinally compressed state when the suture assembly is in its second configuration.

4. A suture assembly according to claim 1 wherein the suture assembly is transformed from its first configuration to its second configuration by pulling the first and second arms of the first suture while holding the bridge of the second suture steady.

5. A suture assembly according to claim 1 wherein the first arm of the second suture terminates in a first end, the second arm of the second suture terminates in a second end, and further wherein the first and second ends are free relative to one another.

6. A suture assembly according to claim 1 wherein the first arm of the second suture comprises a loop which is mounted to the first arm of the first suture, and wherein the second arm of the second suture comprises a loop which is mounted to the second arm of the first suture.

7. A suture assembly according to claim 1 wherein the first and second arms of the second suture are connected to one another so as to form a loop.

8. A suture assembly according to claim 1 wherein the first suture comprises woven suture.

9. A suture assembly according to claim 1 wherein the second suture comprises woven suture.

10. A suture assembly according to claim 1 further comprising a third suture having a generally U-shaped configuration comprising a first arm, a second arm and a bridge connecting the first arm to the second arm, and further wherein the third suture is disposed substantially parallel to the first suture.

11. A suture assembly according to claim 1 wherein the first bridge of the first suture and the second bridge of the second suture face one another.

12. A suture assembly according to claim 1 wherein the first arm and the second arm of each of the first suture and the second suture extend from their respective bridges in opposite directions.

13. A method for attaching an object to an anatomical structure, the method comprising:
providing a suture assembly comprising:
a first suture having a generally U-shaped configuration comprising a first arm, a second arm and a first bridge connecting the first arm of the first suture to the second arm of the first suture;
a second suture comprising a first arm, a second arm and a second bridge connecting the first arm of the second suture to the second arm of the second suture;
the first arm of the second suture being wound helically around the first arm of the first suture in a single first direction, and the second arm of the second suture being wrapped around the second arm of the first suture in a single second, opposite direction;
wherein the first arm of the second suture is wound three times around the first arm of the first suture and the second arm of the second suture is wound three times around the second arm of the first suture;

the suture assembly being capable of assuming (i) a longitudinally-extended, radially-contracted first configuration, and (ii) a longitudinally-contracted, radially-expanded second configuration;

inserting the suture assembly into an opening in the anatomical structure while the suture assembly is in its longitudinally-extended, radially-contracted first configuration, with the first and second arms of the first suture extending from the opening in the anatomical structure; and transforming the suture assembly from its longitudinally-extended, radially-contracted first configuration to its longitudinally-contracted, radially-expanded second configuration in order to secure the suture assembly to the anatomical structure.

14. A method according to claim 13 wherein a portion of the suture assembly has a diameter which is larger than the diameter of the opening in the anatomical structure when the suture assembly is in its longitudinally-contracted, radially-expanded second configuration.

15. A method according to claim 13 wherein the suture assembly is transformed from its longitudinally-extended, radially-contracted first configuration to its longitudinally-contracted, radially-expanded second configuration by moving the wound portions of the second suture along the first and second arms of the first suture.

16. A method according to claim 13 wherein the wound portions of the second suture are in a longitudinally compressed state when the suture assembly is in its second configuration.

17. A method according to claim 13 wherein the suture assembly is transformed from its longitudinally-extended, radially-contracted first configuration to its longitudinally-contracted, radially-expanded second configuration by pulling the first and second arms of the first suture while holding the second bridge of the second suture steady.

18. A method according to claim 13 wherein the suture assembly is inserted into an opening in the anatomical structure while the suture assembly is disposed within a tube.

19. A method according to claim 18 wherein the suture assembly is transformed from its longitudinally-extended, radially-contracted first configuration to its longitudinally-contracted, radially-expanded second configuration after the tube has been withdrawn from the opening formed in the anatomical structure.

20. A method according to claim 18 wherein the suture assembly is transformed from its longitudinally-extended, radially-contracted first configuration to its longitudinally-contracted, radially-expanded second configuration after the suture assembly has been ejected from the tube.

21. A method according to claim 20 wherein the suture assembly is transformed from its longitudinally-extended, radially-contracted first configuration to its longitudinally-contracted, radially-expanded second configuration while the tube is still in the hole formed in the anatomical structure.

22. A method according to claim 18 wherein the suture assembly is compressed within the tube.

23. A method according to claim 13 wherein the first suture comprises woven suture.

24. A method according to claim 13 wherein the second suture comprises woven suture.

25. A method according to claim 13 comprising the additional step of moving a portion of the suture assembly proximally after the suture assembly is in its longitudinally-contracted, radially-expanded second configuration.

26. A method according to claim 25 wherein the anatomical structure comprises bone.

27. A method according to claim 26 wherein the portion of the suture assembly is moved proximally until it engages the underside of a cortical layer of the bone.

28. A method according to claim 13 comprising the additional step of using at least one of the first and second arms of the first suture to secure an object to the anatomical structure.

29. A method according to claim 28 wherein the object comprises soft tissue.

30. A method according to claim 13 wherein the first bridge of the first suture and the second bridge of the second suture face one another.

31. A method according to claim 13 wherein the first arm and the second arm of each of the first suture and the second suture extend from their respective bridges in opposite directions.

32. A system for securing an object to an anatomical structure, the system comprising:

a suture assembly comprising:

a first suture having a generally U-shaped configuration comprising a first arm, a second arm and a first bridge connecting the first arm of the first suture to the second arm of the first suture;

a second suture comprising a first arm, a second arm and a second bridge connecting the first arm of the second suture to the second arm of the second suture;

the first arm of the second suture being wound helically around the first arm of the first suture in a single first direction, and the second arm of the second suture being wound helically around the second arm of the first suture in a single second, opposite direction;

wherein the first arm of the second suture is wound three times around the first arm of the first suture and the second arm of the second suture is wound three times around the second arm of the first suture;

the suture assembly being capable of assuming (i) a longitudinally-extended, radially-contracted first configuration, and (ii) a longitudinally-contracted, radially-expanded second configuration; and an inserter assembly for deploying the suture assembly in the anatomical structure, the inserter assembly comprising:

an insertion tube for carrying at least a portion of the suture assembly within the insertion tube when the suture assembly is in its longitudinally-extended, radially-contracted first configuration; and a push rod for engaging the suture assembly when the suture assembly is disposed within the insertion tube.

33. A system according to claim 32 wherein the inserter assembly is configured so that the push rod can maintain the position of the suture assembly as the insertion tube is withdrawn.

34. A system according to claim 32 wherein the push rod is configured to eject the suture assembly from the insertion tube.

35. A system according to claim 32 wherein the first and second arms of the first suture are releasably connected to the push rod.

36. A system according to claim 35 wherein the push rod is configured to sequentially (i) eject the suture assembly from the tube, and (ii) transform the suture assembly from its longitudinally-extended, radially-contracted first configuration to its longitudinally-contracted, radially-expanded second configuration.

37. A system according to claim 36 wherein the push rod comprises a push rod shaft, a push rod slide mounted to the push rod shaft, and a push rod handle slidably mounted to the push rod slide with a detent mechanism, and further wherein the first and second arms of the first suture are releasably secured to the push rod slide.

38. A system according to claim 32 wherein the inserter assembly can transform the suture assembly without requiring the suture assembly to engage the anatomical structure.

39. A system according to claim 32 wherein the inserter assembly can transform the suture assembly against the distal end of the push rod.

40. A system according to claim 32 wherein the insertion tube shields the suture assembly from contact with the anatomical structure as the suture assembly is inserted into an opening formed in the anatomical structure.

41. A system according to claim 40 wherein the inserter assembly can be introduced into an opening formed in the anatomical structure and then withdrawn from the opening formed in the anatomical structure without deploying the suture assembly from the inserter assembly.

42. A system according to claim 32 wherein the suture assembly is compressed within the insertion tube.

43. A system according to claim 32 wherein the anatomical structure comprises bone.

44. A system according to claim 32 wherein the first bridge of the first suture and the second bridge of the second suture face one another.

45. A system according to claim 32 wherein the first arm and the second arm of each of the first suture and the second suture extend from their respective bridges in opposite directions.

* * * * *